United States Patent
Puré et al.

(10) Patent No.: US 12,139,550 B2
(45) Date of Patent: *Nov. 12, 2024

(54) MONOCLONAL ANTIBODY AGAINST CANINE FIBROBLAST ACTIVATION PROTEIN THAT CROSS-REACTS WITH MOUSE AND HUMAN FIBROBLAST ACTIVATION PROTEIN (FAP)

(71) Applicant: The Trustees of the University of Pennsylvania, Philadelphia, PA (US)

(72) Inventors: Ellen Puré, Bryn Mawr, PA (US); Leslie Todd, Conshohocken, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 365 days.

This patent is subject to a terminal disclaimer.

(21) Appl. No.: 17/029,284

(22) Filed: Sep. 23, 2020

(65) Prior Publication Data
US 2021/0087294 A1 Mar. 25, 2021

Related U.S. Application Data

(60) Provisional application No. 62/904,272, filed on Sep. 23, 2019.

(51) Int. Cl.
*C12N 15/13* (2006.01)
*C07K 16/40* (2006.01)
*G01N 33/569* (2006.01)

(52) U.S. Cl.
CPC ....... *C07K 16/40* (2013.01); *G01N 33/56966* (2013.01); *C07K 2317/33* (2013.01); *C07K 2317/56* (2013.01); *C07K 2317/565* (2013.01); *C07K 2317/622* (2013.01); *G01N 2333/96425* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 9,365,641 | B2 | 6/2016 | June |
| 11,447,570 | B2 | 9/2022 | June |
| 2004/0137513 | A1 | 7/2004 | Devaux |
| 2007/0135998 | A1 | 6/2007 | Van Vlijmen |
| 2011/0052606 | A1 | 3/2011 | Spee |
| 2014/0099340 | A1 | 4/2014 | June |
| 2016/0060356 | A1 | 3/2016 | Bacac |
| 2016/0176964 | A1 | 6/2016 | Arathoon |
| 2016/0194402 | A1 | 7/2016 | Van Eenennaam |
| 2016/0326265 | A1 | 11/2016 | June |
| 2017/0081411 | A1 | 3/2017 | Engels |
| 2017/0226225 | A1 | 8/2017 | Chen |
| 2018/0022822 | A1 | 1/2018 | Brokopp |
| 2019/0167721 | A1 | 6/2019 | Fan |
| 2019/0202902 | A1 | 7/2019 | Chen |

FOREIGN PATENT DOCUMENTS

| | | | |
|---|---|---|---|
| WO | 2000029584 | | 5/2000 |
| WO | 2005011376 | | 2/2005 |
| WO | WO 2011/040972 | * | 4/2011 |
| WO | 2013117761 | | 8/2013 |
| WO | 2014055442 A2 | | 4/2014 |
| WO | 2014184194 | | 11/2014 |
| WO | 2015032906 | | 3/2015 |
| WO | 2015090229 A1 | | 6/2015 |
| WO | 2016070050 | | 5/2016 |
| WO | 2017181119 | | 10/2017 |
| WO | 2018105560 | | 6/2018 |
| WO | 2018148440 A1 | | 8/2018 |
| WO | 2019067425 | | 4/2019 |
| WO | 2019126724 | | 6/2019 |
| WO | 2019173291 | | 9/2019 |
| WO | 2021061708 | | 4/2021 |
| WO | 2021061778 | | 4/2021 |
| WO | 2022081694 | | 4/2022 |

OTHER PUBLICATIONS

Tillmanns, J. et al., "Fibroblast activation protein alpha expression identifies activated fibroblasts after myocardial infarction," J Mol Cell Cardiol, 87:194-203 (2015).
Wang, Liang-Chuan et al., "Targeting Fibroblast Activation Protein in Tumor Stroma with Chimeric Antigen Receptor T Cells Can Inhibit Tumor Growth and Augment Host Immunity Without Severe Toxicity<" Cancer Immunol Res 2(2):154-166 (Feb. 2014).
Lo, A. et al., "Tumor-Promoting Desmoplasia Is Disrupted by Depleting FAP-Expressing Stromal Cells," Cancer Res, 75(14): 2800-2810 (2015).
Aghajanian, H. et al., "Targeting cardiac fibrosis with engineered T cells," Nature, 573:430-433 (Sep. 19, 2019).
Roberts, E. W., et al., "Depletion of stromal cells expressing fibroblast activation protein-[alpha] from skeletal muscle and bone marrow results in cachexia and anemia," J. Exp. Med., vol. 210, No. 6 :1137-1151 (2013).
Cartellier et al., "Chimeric Antigen Receptor-Engineered T Cells for Immunotherapy of Cancer," J Biomed Biotechnol, vol. 2010, Articel ID 956304, pp. 1-13 (2010).
Petrausch, Ulf et al., "Re-directed T cells for the treatment of fibroblast activation protein (FAP)-positive malignant pleural mesothelioma (FAPME-1)," BMC Cancer, 12:615, pp. 1-7 (Dec. 22, 2012).
Shah, Ami et al., "Heart Failure: A Class Review of Pharmacotherapy," P&T, vol. 42, No. 7, pp. 464-472 (Jul. 1, 2017).

(Continued)

*Primary Examiner* — Christine J Saoud
(74) *Attorney, Agent, or Firm* — Saul Ewing LLP; Kathryn Doyle

(57) ABSTRACT

The present invention relates to antibodies, binding polypeptides, and scFvs specific for fibroblast activation protein (FAP) capable of cross reacting with canine, mouse, and human FAP.

11 Claims, 6 Drawing Sheets

Specification includes a Sequence Listing.

(56) References Cited

OTHER PUBLICATIONS

Geyer, Mark B. et al. Review: Current clinical applications of chimeric antigen receptor (CAR) modified T cells, Cytotherapy, vol. 18, No. 11, pp. 1393-1409 (Nov. 2016).

Extended European Search Report, dated of completion Dec. 13, 2021, for European Application No. 18861807.8.

Sun, S. et al., "Immunotherapy with CAR-Modified T Cells: Toxicities and Overcoming Strategies", Immunotherapy and Vaccine Development, vol. 2018, pp. 1-10 (Apr. 17, 2018,).

Wang, L-C. S. et al., "Targeting fibroblast activation protein in tumor stroma with chimeric antigen receptor T cells can inhibit tumor growth and augment host immunity without severe toxicity", Cancer Immunol Res, 2(2):154-166 (2014).

Kaur, H. et al., "Targeted Ablation of Periostin-Expressing Activated Fibroblasts Prevents Adverse Cardiac Remodeling in Mice", Circ Res, 118(12):1906-1917 (2016).

Brocks, Bodo et al., 'Species-Crossreactive scFv Against the Tumor Stroma Marker "Fibroblast Activation Protein" Selected by Phage Display From an Immunized FAP -/- Knock-Out Mouse,' Molecular Medicine 7(7): 461-469 (2001).

Xia, A-L, et al., "Chimeric-antigen receptor T (CAR-T) cell therapy for solid tumors: challenges and opportunities", vol. 8, No. 52, pp. 90521-09531, 2017.

Mata, M. et al., "Adapting the Spontaneous Canine Osteosarcoma Model for T-Cell Therapy," vol. 21, Suppl. 1, S154, 400 (2013).

Giuliano, A. et al., "Expression of Fibroblast Activating Protein and Correlation with Histological Grade, Mitotic Index and Ki67 Expression in Canine Mast Cell Tumours," J Comp Pathol, 156(1):14-20 (Jan. 2017) (Epub Nov. 24, 2016).

\* cited by examiner

FIG. 1

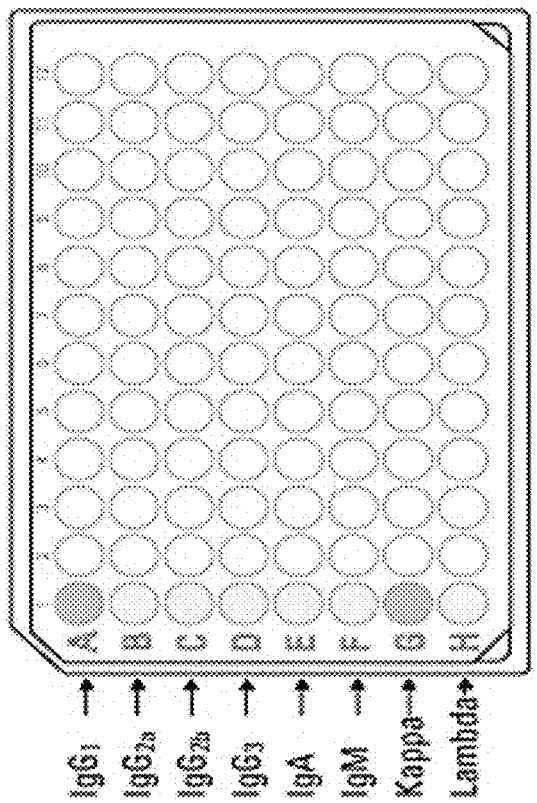
FIG. 4C
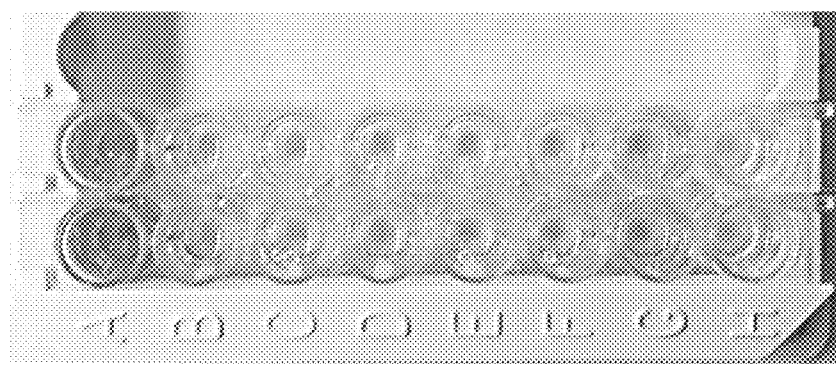
FIG. 4B
| Isotyping (Thermo Fisher Rapid ELISA Mouse mAb Isotyping Kit #37503) | | |
|---|---|---|
| Run information | | |
| A | 2.30701 | 2.05944 |
| B | 0.128739 | 0.134897 |
| C | 0.061526 | 0.083605 |
| D | 0.053079 | 0.070057 |
| E | 0.054464 | 0.074575 |
| F | 0.048878 | 0.064709 |
| G | 0.280926 | 0.302431 |
| H | 0.05484 | 0.067141 |
FIG. 4A

SEQUENCE LISTING

<160> NUMBER OF SEQ ID NOS: 43

<210> SEQ ID NO 1
<211> LENGTH: 9
<212> TYPE: PRT
<213> ORGANISM: Artificial Sequence
<220> FEATURE:
<223> OTHER INFORMATION: 4G5 HCDR1

<400> SEQUENCE: 1

Tyr Thr Ile Thr Ser Tyr Ser Leu His
1               5

<210> SEQ ID NO 2
<211> LENGTH: 18
<212> TYPE: PRT
<213> ORGANISM: Artificial Sequence
<220> FEATURE:
<223> OTHER INFORMATION: 4G5 HCDR2

<400> SEQUENCE: 2

Glu Ile Asn Pro Ala Asn Gly Asp His Asn Phe Ser Glu Lys Phe Glu
1               5                   10                  15

Ile Lys

<210> SEQ ID NO 3
<211> LENGTH: 12
<212> TYPE: PRT
<213> ORGANISM: Artificial Sequence
<220> FEATURE:
<223> OTHER INFORMATION: 4G5 HCDR3

<400> SEQUENCE: 3

Leu Asp Asp Ser Arg Phe His Trp Tyr Phe Asp Val
1               5                   10

<210> SEQ ID NO 4
<211> LENGTH: 10
<212> TYPE: PRT
<213> ORGANISM: Artificial Sequence
<220> FEATURE:
<223> OTHER INFORMATION: 4G5 LCDR1

<400> SEQUENCE: 4

Thr Ala Ser Ser Ser Val Ser Tyr Met Tyr
1               5                   10

<210> SEQ ID NO 5
<211> LENGTH: 6
<212> TYPE: PRT
<213> ORGANISM: Artificial Sequence
<220> FEATURE:
<223> OTHER INFORMATION: 4G5 LCDR2

<400> SEQUENCE: 5

Leu Thr Ser Asn Leu Ala
1               5

<210> SEQ ID NO 6
<211> LENGTH: 10
<212> TYPE: PRT
<213> ORGANISM: Artificial Sequence
<220> FEATURE:
<223> OTHER INFORMATION: 4G5 LCDR3

<400> SEQUENCE: 6

Gln Gln Trp Ser Gly Tyr Pro Pro Ile Thr
1               5                   10

<210> SEQ ID NO 7
<211> LENGTH: 121
<212> TYPE: PRT
<213> ORGANISM: Artificial Sequence
<220> FEATURE:
<223> OTHER INFORMATION: 4G5 VH

<400> SEQUENCE: 7

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Ile Thr Ser Tyr
            20                  25                  30

Ser Leu His Trp Val Lys Gln Arg Pro Gly Gln Gly Leu Glu Trp Ile
        35                  40                  45

Gly Glu Ile Asn Pro Ala Asn Gly Asp His Asn Phe Ser Glu Lys Phe
    50                  55                  60

Glu Ile Lys Ala Thr Leu Thr Val Asp Ser Ser Asn Thr Ala Phe
65                  70                  75                  80

Met Gln Leu Ser Arg Leu Thr Ser Glu Asp Ser Ala Val Tyr Tyr Cys
                85                  90                  95

Thr Arg Leu Asp Asp Ser Arg Phe His Trp Tyr Phe Asp Val Trp Gly
            100                 105                 110

Ala Gly Thr Thr Val Thr Val Ser Ser
        115                 120

<210> SEQ ID NO 8
<211> LENGTH: 363
<212> TYPE: DNA
<213> ORGANISM: Artificial Sequence
<220> FEATURE:
<223> OTHER INFORMATION: 4G5 VH

<400> SEQUENCE: 8
caggtccaac tgcagcagcc tggggctgaa ctggtaaagc ctggggcttc agtgaagttg     60
tcctgcaagg cgtctggcta caccatcacc agctactctc tgcactgggt gaagcagagg    120
cctggacaag ccttgagtg gattggagag attaatcctg ccaatggtga tcataacttc     180
agtgagaagt tcgagatcaa ggccacactg actgtagaca gctcctccaa cacagcattc    240
atgcaactca gcaggctgac atctgaggac tctgcggtct attactgtac aagattggac    300
gatagtaggt tccactggta cttcgatgtc tggggcgcag ggaccacggt caccgtctcc    360
tca                                                                  363

<210> SEQ ID NO 9
<211> LENGTH: 107
<212> TYPE: PRT
<213> ORGANISM: Artificial Sequence
<220> FEATURE:
<223> OTHER INFORMATION: 4G5 VL

<400> SEQUENCE: 9

Gln Ile Val Leu Thr Gln Ser Pro Ala Leu Met Ser Ala Ser Pro Gly
1               5                   10                  15

Glu Lys Val Thr Met Thr Cys Thr Ala Ser Ser Ser Val Ser Tyr Met
            20                  25                  30

Tyr Trp Tyr Gln Gln Lys Pro Arg Ser Ser Pro Lys Pro Trp Ile Phe
        35                  40                  45

```
Leu Thr Ser Asn Leu Ala Ser Gly Val Pro Ala Arg Phe Ser Gly Arg
        50                  55                  60

Gly Ser Gly Thr Ser Phe Ser Leu Thr Ile Ser Ser Met Glu Ala Glu
 65                  70                  75                  80

Asp Ala Ala Thr Tyr Tyr Cys Gln Gln Trp Ser Gly Tyr Pro Pro Ile
                85                  90                  95

Thr Phe Gly Ser Gly Thr Lys Leu Glu Ile Lys
            100                 105

<210> SEQ ID NO 10
<211> LENGTH: 321
<212> TYPE: DNA
<213> ORGANISM: Artificial Sequence
<220> FEATURE:
<223> OTHER INFORMATION: 4G5 VL

<400> SEQUENCE: 10
caaattgttc tcacccagtc tccagcgctc atgtctgctt ctccagggga gaaggtcacc      60
atgacctgca ctgccagctc aagtgttagt tacatgtact ggtaccagca gaagccacga     120
tcctccccca aaccctggat ttttctcacc tccaacctgg cttctggagt ccctgctcgc     180
ttcagtggcc gtgggtctgg gacctctttc tctctcacaa tcagcagcat ggaggctgaa     240
gatgctgcca cttattactg ccagcagtgg agtggttacc cacccatcac attcggctcg     300
gggacaaagt tggaaataaa a                                               321

<210> SEQ ID NO 11
<211> LENGTH: 243
<212> TYPE: PRT
<213> ORGANISM: Artificial Sequence
<220> FEATURE:
<223> OTHER INFORMATION: 4G5 scFv VLVH

<400> SEQUENCE: 11

Gln Ile Val Leu Thr Gln Ser Pro Ala Leu Met Ser Ala Ser Pro Gly
 1               5                  10                  15

Glu Lys Val Thr Met Thr Cys Thr Ala Ser Ser Ser Val Ser Tyr Met
                20                  25                  30

Tyr Trp Tyr Gln Gln Lys Pro Arg Ser Ser Pro Lys Pro Trp Ile Phe
            35                  40                  45

Leu Thr Ser Asn Leu Ala Ser Gly Val Pro Ala Arg Phe Ser Gly Arg
        50                  55                  60

Gly Ser Gly Thr Ser Phe Ser Leu Thr Ile Ser Ser Met Glu Ala Glu
 65                  70                  75                  80

Asp Ala Ala Thr Tyr Tyr Cys Gln Gln Trp Ser Gly Tyr Pro Pro Ile
                85                  90                  95

Thr Phe Gly Ser Gly Thr Lys Leu Glu Ile Lys Gly Gly Gly Gly Ser
            100                 105                 110

Gly Gly Gly Gly Ser Gly Gly Gly Ser Gln Val Gln Leu Gln Gln
        115                 120                 125

Pro Gly Ala Glu Leu Val Lys Pro Gly Ala Ser Val Lys Leu Ser Cys
    130                 135                 140

Lys Ala Ser Gly Tyr Thr Ile Thr Ser Tyr Leu His Trp Val Lys
145                 150                 155                 160

Gln Arg Pro Gly Gln Gly Leu Glu Trp Ile Gly Glu Ile Asn Pro Ala
                165                 170                 175

Asn Gly Asp His Asn Phe Ser Glu Lys Phe Glu Ile Lys Ala Thr Leu
```

```
                180                185                190
Thr Val Asp Ser Ser Asn Thr Ala Phe Met Gln Leu Ser Arg Leu
            195                200                205

Thr Ser Glu Asp Ser Ala Val Tyr Tyr Cys Thr Arg Leu Asp Asp Ser
        210                215                220

Arg Phe His Trp Tyr Phe Asp Val Trp Gly Ala Gly Thr Thr Val Thr
225                230                235                240

Val Ser Ser

<210> SEQ ID NO 12
<211> LENGTH: 729
<212> TYPE: DNA
<213> ORGANISM: Artificial Sequence
<220> FEATURE:
<223> OTHER INFORMATION: 4G5 scFv VLVH

<400> SEQUENCE: 12
caaattgttc tcacccagtc tccagcgctc atgtctgctt ctccagggga gaaggtcacc      60
atgacctgca ctgccagctc aagtgttagt tacatgtact ggtaccagca gaagccacga    120
tcctccccca aaccctggat ttttctcacc tccaacctgg cttctggagt ccctgctcgc    180
ttcagtggcc gtgggtctgg gacctctttc tctctcacaa tcagcagcat ggaggctgaa    240
gatgctgcca cttattactg ccagcagtgg agtggttacc cacccatcac attcggctcg    300
gggacaaagt tggaaataaa aggtggaggt ggcagcggag gaggtgggtc cggcggtgga    360
ggaagccagg tccaactgca gcagcctggg gctgaactgg taaagcctgg ggcttcagtg    420
aagttgtcct gcaaggcgtc tggctacacc atcaccagct actctctgca ctgggtgaag    480
cagaggcctg gacaaggcct tgagtggatt ggagagatta atcctgccaa tggtgatcat    540
aacttcagtg agaagttcga gatcaaggcc acactgactg tagacagctc ctccaacaca    600
gcattcatgc aactcagcag gctgacatct gaggactctg cggtctatta ctgtacaaga    660
ttggacgata gtaggttcca ctggtacttc gatgtctggg gcgcagggac cacggtcacc    720
gtctcctca                                                             729

<210> SEQ ID NO 13
<211> LENGTH: 243
<212> TYPE: PRT
<213> ORGANISM: Artificial Sequence
<220> FEATURE:
<223> OTHER INFORMATION: 4G5 scFv VHVL

<400> SEQUENCE: 13

Gln Val Gln Leu Gln Gln Pro Gly Ala Glu Leu Val Lys Pro Gly Ala
1               5                  10                  15

Ser Val Lys Leu Ser Cys Lys Ala Ser Gly Tyr Thr Ile Thr Ser Tyr
            20                  25                  30

Ser Leu His Trp Val Lys Gln Arg Pro Gly Gln Gly Leu Glu Trp Ile
        35                  40                  45

Gly Glu Ile Asn Pro Ala Asn Gly Asp His Asn Phe Ser Glu Lys Phe
    50                  55                  60

Glu Ile Lys Ala Thr Leu Thr Val Asp Ser Ser Asn Thr Ala Phe
65                  70                  75                  80

Met Gln Leu Ser Arg Leu Thr Ser Glu Asp Ser Ala Val Tyr Tyr Cys
                85                  90                  95

Thr Arg Leu Asp Asp Ser Arg Phe His Trp Tyr Phe Asp Val Trp Gly
            100                 105                 110
```

Ala Gly Thr Thr Val Thr Val Ser Ser Gly Gly Gly Ser Gly Gly
        115                 120                 125

Gly Gly Ser Gly Gly Gly Ser Gln Ile Val Leu Thr Gln Ser Pro
        130                 135                 140

Ala Leu Met Ser Ala Ser Pro Gly Glu Lys Val Thr Met Thr Cys Thr
145                 150                 155                 160

Ala Ser Ser Ser Val Ser Tyr Met Tyr Trp Tyr Gln Gln Lys Pro Arg
                165                 170                 175

Ser Ser Pro Lys Pro Trp Ile Phe Leu Thr Ser Asn Leu Ala Ser Gly
                180                 185                 190

Val Pro Ala Arg Phe Ser Gly Arg Gly Ser Gly Thr Ser Phe Ser Leu
            195                 200                 205

Thr Ile Ser Ser Met Glu Ala Glu Asp Ala Ala Thr Tyr Tyr Cys Gln
        210                 215                 220

Gln Trp Ser Gly Tyr Pro Pro Ile Thr Phe Gly Ser Gly Thr Lys Leu
225                 230                 235                 240

Glu Ile Lys

<210> SEQ ID NO 14
<211> LENGTH: 729
<212> TYPE: DNA
<213> ORGANISM: Artificial Sequence
<220> FEATURE:
<223> OTHER INFORMATION: 4G5 scFv VHVL

<400> SEQUENCE: 14
caggtccaac tgcagcagcc tggggctgaa ctggtaaagc ctggggcttc agtgaagttg      60
tcctgcaagg cgtctggcta caccatcacc agctactctc tgcactgggt gaagcagagg     120
cctggacaag gccttgagtg gattggagag attaatcctg ccaatggtga tcataacttc     180
agtgagaagt tcgagatcaa ggccacactg actgtagaca gctcctccaa cacagcattc     240
atgcaactca gcaggctgac atctgaggac tctgcggtct attactgtac aagattggac     300
gatagtaggt tccactggta cttcgatgtc tggggcgcag ggaccacggt caccgtctcc     360
tcaggtggag gtggcagcgg aggaggtggg tccggcggtg aggaagccaa aattgttctc     420
acccagtctc cagcgctcat gtctgcttct caggggagaa aggtcaccat gacctgcact     480
gccagctcaa gtgttagtta catgtactgg taccagcaga agccacgatc ctcccccaaa     540
ccctggattt ttctcacctc caacctggct tctggagtcc ctgctcgctt cagtggccgt     600
gggtctggga cctctttctc tctcacaatc agcagcatgg aggctgaaga tgctgccact     660
tattactgcc agcagtggag tggttaccca cccatcacat tcggctcggg gacaaagttg     720
gaaataaaa                                                             729

<210> SEQ ID NO 15
<211> LENGTH: 15
<212> TYPE: PRT
<213> ORGANISM: Artificial Sequence
<220> FEATURE:
<223> OTHER INFORMATION: Linker

<400> SEQUENCE: 15

Gly Gly Gly Gly Ser Gly Gly Gly Gly Ser Gly Gly Gly Gly Ser
1               5                   10                  15

<210> SEQ ID NO 16
<211> LENGTH: 2283

```
<212> TYPE: DNA
<213> ORGANISM: Artificial Sequence
<220> FEATURE:
<223> OTHER INFORMATION: Full Length Canine FAP

<400> SEQUENCE: 16
```

| | | | | | |
|---|---|---|---|---|---|
| atgaagacgt | ggttaaaaat | tgtatttgga | gttgccacct | ctgctgtgct | tgctttattg | 60 |
| gtgatgtgca | ttgtcttacg | tccttcaaga | gttcatgact | ccgaaggagg | tacaacaaga | 120 |
| gcactcacac | tggaggatat | tttaaatggg | acatttacct | ataaaacatt | ttttccaaac | 180 |
| tggatttcag | acaagaata | tcttcatcag | tctacagata | tgatatagt | atattacaat | 240 |
| attgaaacag | gagaatcata | taccattttg | agtaatgcca | ccatgaaaag | tgtgaatgct | 300 |
| tcaaattatg | gcttatcacc | tgatcgtcaa | tttgcatatc | tagaaagtga | ttattcaaag | 360 |
| ctttggagat | actcttacac | tgcaacatat | cacatctata | acctcaataa | tggagagttt | 420 |
| ataagaagaa | atgagcttcc | tcgtccaatt | cagtatttat | gctggtcgcc | tgttgggagt | 480 |
| aaattagcat | atgtctatca | aaacaatatc | tatttgaaac | aaagaccaga | agacccacct | 540 |
| tttcaaataa | catataatgg | aagagaaaat | aaaatattca | atggaatccc | agactgggta | 600 |
| tatgaagagg | aaatgcttgc | tacaaaacat | gctctctggt | ggtctcctaa | tggaaaattt | 660 |
| ttggcatatg | cagaatttaa | tgatacagag | ataccagtta | ttgcctattc | ctattatggt | 720 |
| gatgaacaat | atcctagaac | aataaatatt | ccatacccaa | aggctggagc | taagaaccct | 780 |
| gttgttcgga | tctttattat | cgataccact | tatcctcagc | agacaggtcc | cagagaagtg | 840 |
| ccagttccag | caatgatagc | atcaagtgat | tattatttca | gttggctcac | atgggttact | 900 |
| gatgaacgag | tatgtttgca | gtggctaaaa | agaatccaga | acgtttcagt | tctgtccata | 960 |
| tgtgatttca | gggaaggctg | gcagacatgg | gattgtccaa | aggcccagga | acatatagaa | 1020 |
| gaaagcagaa | ctggatgggc | tggtggattc | tttgtttcaa | caccagtttt | cagctatgat | 1080 |
| gccatttcat | actacaaaat | atttagcgac | aaggatggct | acaaacatat | tcactatatc | 1140 |
| aaagacactg | tggaaaatgc | tattcaaatt | acaagtggca | agtgggaggc | ataaaatata | 1200 |
| ttcagagtaa | cacaggattc | actgttttat | tctagcaatg | aatttgaaga | ctacccagga | 1260 |
| agaagaaata | tctatagaat | tagcattgga | agctctcctc | caagcaaaaa | gtgcattact | 1320 |
| tgccatctaa | ggaagaaag | gtgccaatat | tacacagcaa | gtttcagtga | ctacgccaag | 1380 |
| tactatgcac | ttatctgcta | tggcccaggc | ctccccattt | ccaccttca | tgacggccac | 1440 |
| actgatcaag | aaattaaaat | cctggaagaa | aacaaagaat | tggaaaatgc | tttgaaaaat | 1500 |
| atccagctgc | ctaaagagga | aattaagaaa | cttgaagtgg | atgatattac | tttatggtac | 1560 |
| aagatgatgc | ttcctccccg | gtttgacaga | tcaaagaagt | atcccttgct | aattcaagtg | 1620 |
| tatggtggtc | cctgcagtca | gagcgtaaag | tctgtattca | gtattaattg | gatttcttat | 1680 |
| cttgcaagta | aggaagggat | agtcattgcc | ttggtggatg | gccgaggaac | agcttaccaa | 1740 |
| ggtgacaaac | tcctgtatgc | agtatatcga | aagctgggtg | tttatgaagt | tgaggaccag | 1800 |
| atcacagccg | tcagaaaatt | catagaaatg | ggtttcattg | atgaaaaag | aatagccata | 1860 |
| tggggctggt | cctatggagg | ctatgtttca | tcactggccc | ttgcttcagg | aactggtctt | 1920 |
| ttcaaatgtg | gatagcagt | ggctcctgtc | tccagctggg | aatattacgc | atctatctac | 1980 |
| acagaacgat | tcatgggcct | cccaacaaag | aacgataatc | tcgagcacta | caaaaattca | 2040 |
| actgtgatgg | caagagcaga | atatttcaga | aatgtagact | atcttctcat | ccacggaaca | 2100 |
| gcagatgata | atgtgcactt | tcaaaaactca | gcacagattg | ctaaagctct | ggttaatgca | 2160 |

```
caagtggatt tccaggcaat gtggtactct gaccagaacc atggcatacc cggcctgtcc    2220
tcgaagcact tatatacccg catgacccac ttcctaaagc agtgttttc tttgtccgac     2280 tga                                                                 2283
```

<210> SEQ ID NO 17
<211> LENGTH: 10
<212> TYPE: PRT
<213> ORGANISM: Artificial Sequence
<220> FEATURE:
<223> OTHER INFORMATION: 4G5 HCDR1

<400> SEQUENCE: 17

Gly Tyr Thr Ile Thr Ser Tyr Ser Leu His
1               5                   10

<210> SEQ ID NO 18
<211> LENGTH: 20
<212> TYPE: PRT
<213> ORGANISM: Artificial Sequence
<220> FEATURE:
<223> OTHER INFORMATION: 4G5 HCDR2

<400> SEQUENCE: 18

Glu Ile Asn Pro Ala Asn Gly Asp His Asn Phe Ser Glu Lys Phe Glu
1               5                   10                  15

Ile Lys Ala Thr
            20

<210> SEQ ID NO 19
<211> LENGTH: 14
<212> TYPE: PRT
<213> ORGANISM: Artificial Sequence
<220> FEATURE:
<223> OTHER INFORMATION: 4G5 HCDR3

<400> SEQUENCE: 19

Thr Arg Leu Asp Asp Ser Arg Phe His Trp Tyr Phe Asp Val
1               5                   10

<210> SEQ ID NO 20
<211> LENGTH: 7
<212> TYPE: PRT
<213> ORGANISM: Artificial Sequence
<220> FEATURE:
<223> OTHER INFORMATION: 4G5 LCDR2

<400> SEQUENCE: 20

Leu Thr Ser Asn Leu Ala Ser
1               5

<210> SEQ ID NO 21
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: repeat n times, where n represents an integer
      of at least 1

<400> SEQUENCE: 21

Gly Ser Gly Gly Ser
1               5

```
<210> SEQ ID NO 22
<211> LENGTH: 4
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(4)
<223> OTHER INFORMATION: repeat n times, where n represents an integer
      of at least 1

<400> SEQUENCE: 22

Gly Gly Gly Ser
1

<210> SEQ ID NO 23
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: repeat n times, where n represents an integer
      of at least 1

<400> SEQUENCE: 23

Gly Gly Gly Gly Ser
1               5

<210> SEQ ID NO 24
<211> LENGTH: 4
<212> TYPE: PRT
<213> ORGANISM: Artificial Sequence
<220> FEATURE:
<223> OTHER INFORMATION: Linker

<400> SEQUENCE: 24

Gly Gly Ser Gly
1

<210> SEQ ID NO 25
<211> LENGTH: 5
<212> TYPE: PRT
<213> ORGANISM: Artificial Sequence
<220> FEATURE:
<223> OTHER INFORMATION: Linker

<400> SEQUENCE: 25

Gly Gly Ser Gly Gly
1               5

<210> SEQ ID NO 26
<211> LENGTH: 5
<212> TYPE: PRT
<213> ORGANISM: Artificial Sequence
<220> FEATURE:
<223> OTHER INFORMATION: Linker

<400> SEQUENCE: 26

Gly Ser Gly Ser Gly
1               5

<210> SEQ ID NO 27
<211> LENGTH: 5
<212> TYPE: PRT
```

-continued

```
<213> ORGANISM: Artificial Sequence
<220> FEATURE:
<223> OTHER INFORMATION: Linker

<400> SEQUENCE: 27

Gly Ser Gly Gly Gly
1               5

<210> SEQ ID NO 28
<211> LENGTH: 5
<212> TYPE: PRT
<213> ORGANISM: Artificial Sequence
<220> FEATURE:
<223> OTHER INFORMATION: Linker

<400> SEQUENCE: 28

Gly Gly Gly Ser Gly
1               5

<210> SEQ ID NO 29
<211> LENGTH: 5
<212> TYPE: PRT
<213> ORGANISM: Artificial Sequence
<220> FEATURE:
<223> OTHER INFORMATION: Linker

<400> SEQUENCE: 29

Gly Ser Ser Ser Gly
1               5

<210> SEQ ID NO 30
<211> LENGTH: 5
<212> TYPE: PRT
<213> ORGANISM: Artificial Sequence
<220> FEATURE:
<223> OTHER INFORMATION: Linker

<400> SEQUENCE: 30

Gly Gly Gly Gly Ser
1               5

<210> SEQ ID NO 31
<211> LENGTH: 45
<212> TYPE: DNA
<213> ORGANISM: Artificial Sequence
<220> FEATURE:
<223> OTHER INFORMATION: Linker

<400> SEQUENCE: 31
ggtggcggtg gctcgggcgg tggtgggtcg ggtggcggcg gatct            45

<210> SEQ ID NO 32
<211> LENGTH: 4
<212> TYPE: PRT
<213> ORGANISM: Artificial Sequence
<220> FEATURE:
<223> OTHER INFORMATION: Furin cleavage site
<220> FEATURE:
<221> NAME/KEY: variant
<222> LOCATION: (2)..(2)
<223> OTHER INFORMATION: Xaa can be any naturally occurring amino acid

<400> SEQUENCE: 32

Arg Xaa Lys Arg
1

<210> SEQ ID NO 33
```

<211> LENGTH: 4
<212> TYPE: PRT
<213> ORGANISM: Artificial Sequence
<220> FEATURE:
<223> OTHER INFORMATION: Furin cleavage site
<220> FEATURE:
<221> NAME/KEY: variant
<222> LOCATION: (2)..(2)
<223> OTHER INFORMATION: Xaa can be any naturally occurring amino acid

<400> SEQUENCE: 33

Arg Xaa Arg Arg
1

<210> SEQ ID NO 34
<211> LENGTH: 5
<212> TYPE: PRT
<213> ORGANISM: Artificial Sequence
<220> FEATURE:
<223> OTHER INFORMATION: Furin cleavage site
<220> FEATURE:
<221> NAME/KEY: variant
<222> LOCATION: (1)..(1)
<223> OTHER INFORMATION: Xaa can be any naturally occurring amino acid
<220> FEATURE:
<221> NAME/KEY: variant
<222> LOCATION: (3)..(4)
<223> OTHER INFORMATION: Xaa can be any naturally occurring amino acid

<400> SEQUENCE: 34

Xaa Arg Xaa Xaa Arg
1 5

<210> SEQ ID NO 35
<211> LENGTH: 4
<212> TYPE: PRT
<213> ORGANISM: Artificial Sequence
<220> FEATURE:
<223> OTHER INFORMATION: Furin cleavage site
<220> FEATURE:
<221> NAME/KEY: variant
<222> LOCATION: (2)..(3)
<223> OTHER INFORMATION: Xaa can be any naturally occurring amino acid

<400> SEQUENCE: 35

Arg Xaa Xaa Arg
1

<210> SEQ ID NO 36
<211> LENGTH: 4
<212> TYPE: PRT
<213> ORGANISM: Artificial Sequence
<220> FEATURE:
<223> OTHER INFORMATION: Furin cleavage site

<400> SEQUENCE: 36

Arg Gln Lys Arg
1

<210> SEQ ID NO 37
<211> LENGTH: 22
<212> TYPE: DNA
<213> ORGANISM: Artificial Sequence
<220> FEATURE:
<223> OTHER INFORMATION: Primer

<400> SEQUENCE: 37
atgtagacgt ggttaaaaat tg 22

-continued

```
<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
cgtcatcttc agtcggacaa                                                  20

<210> SEQ ID NO 39
<211> LENGTH: 760
<212> TYPE: PRT
<213> ORGANISM: Canis lupus familiaris
<220> FEATURE:
<223> OTHER INFORMATION: FAP protein

<400> SEQUENCE: 39
```

| | | | | | | | | | | | | | | |
|---|---|---|---|---|---|---|---|---|---|---|---|---|---|---|
| Met | Lys | Thr | Trp | Leu | Lys | Ile | Val | Phe | Gly | Val | Ala | Thr | Ser | Ala | Val |
| 1 | | | | 5 | | | | | 10 | | | | | 15 | |
| Leu | Ala | Leu | Leu | Val | Met | Cys | Ile | Val | Leu | Arg | Pro | Ser | Arg | Val | His |
| | | | 20 | | | | | 25 | | | | | 30 | | |
| Asp | Ser | Glu | Gly | Gly | Thr | Thr | Arg | Ala | Leu | Thr | Leu | Glu | Asp | Ile | Leu |
| | | 35 | | | | | 40 | | | | | 45 | | | |
| Asn | Gly | Thr | Phe | Thr | Tyr | Lys | Thr | Phe | Phe | Pro | Asn | Trp | Ile | Ser | Gly |
| 50 | | | | | 55 | | | | | 60 | | | | | |
| Gln | Glu | Tyr | Leu | His | Gln | Ser | Thr | Asp | Asn | Asp | Ile | Val | Tyr | Tyr | Asn |
| 65 | | | | | 70 | | | | | 75 | | | | | 80 |
| Ile | Glu | Thr | Gly | Glu | Ser | Tyr | Thr | Ile | Leu | Ser | Asn | Ala | Thr | Met | Lys |
| | | | | 85 | | | | | 90 | | | | | 95 | |
| Ser | Val | Asn | Ala | Ser | Asn | Tyr | Gly | Leu | Ser | Pro | Asp | Arg | Gln | Phe | Ala |
| | | | 100 | | | | | 105 | | | | | 110 | | |
| Tyr | Leu | Glu | Ser | Asp | Tyr | Ser | Lys | Leu | Trp | Arg | Tyr | Ser | Tyr | Thr | Ala |
| | | | 115 | | | | | 120 | | | | | 125 | | |
| Thr | Tyr | His | Ile | Tyr | Asn | Leu | Asn | Asn | Gly | Glu | Phe | Ile | Arg | Arg | Asn |
| | | 130 | | | | | 135 | | | | | 140 | | | |
| Glu | Leu | Pro | Arg | Pro | Ile | Gln | Tyr | Leu | Cys | Trp | Ser | Pro | Val | Gly | Ser |
| 145 | | | | | 150 | | | | | 155 | | | | | 160 |
| Lys | Leu | Ala | Tyr | Val | Tyr | Gln | Asn | Asn | Ile | Tyr | Leu | Lys | Gln | Arg | Pro |
| | | | | 165 | | | | | 170 | | | | | 175 | |
| Glu | Asp | Pro | Pro | Phe | Gln | Ile | Thr | Tyr | Asn | Gly | Arg | Glu | Asn | Lys | Ile |
| | | | 180 | | | | | 185 | | | | | 190 | | |
| Phe | Asn | Gly | Ile | Pro | Asp | Trp | Val | Tyr | Glu | Glu | Glu | Met | Leu | Ala | Thr |
| | | | 195 | | | | | 200 | | | | | 205 | | |
| Lys | His | Ala | Leu | Trp | Trp | Ser | Pro | Asn | Gly | Lys | Phe | Leu | Ala | Tyr | Ala |
| | | 210 | | | | | 215 | | | | | 220 | | | |
| Glu | Phe | Asn | Asp | Thr | Glu | Ile | Pro | Val | Ile | Ala | Tyr | Ser | Tyr | Tyr | Gly |
| 225 | | | | | 230 | | | | | 235 | | | | | 240 |
| Asp | Glu | Gln | Tyr | Pro | Arg | Thr | Ile | Asn | Ile | Pro | Tyr | Pro | Lys | Ala | Gly |
| | | | | 245 | | | | | 250 | | | | | 255 | |
| Ala | Lys | Asn | Pro | Val | Val | Arg | Ile | Phe | Ile | Ile | Asp | Thr | Thr | Tyr | Pro |
| | | | 260 | | | | | 265 | | | | | 270 | | |
| Gln | Gln | Thr | Gly | Pro | Arg | Glu | Val | Pro | Val | Pro | Ala | Met | Ile | Ala | Ser |
| | | | 275 | | | | | 280 | | | | | 285 | | |
| Ser | Asp | Tyr | Tyr | Phe | Ser | Trp | Leu | Thr | Trp | Val | Thr | Asp | Glu | Arg | Val |
| | | 290 | | | | | 295 | | | | | 300 | | | |
| Cys | Leu | Gln | Trp | Leu | Lys | Arg | Ile | Gln | Asn | Val | Ser | Val | Leu | Ser | Ile |

```
            305                 310                 315                 320
Cys Asp Phe Arg Glu Gly Trp Gln Thr Trp Asp Cys Pro Lys Ala Gln
                325                 330                 335

Glu His Ile Glu Glu Ser Arg Thr Gly Trp Ala Gly Gly Phe Phe Val
                340                 345                 350

Ser Thr Pro Val Phe Ser Tyr Asp Ala Ile Ser Tyr Lys Ile Phe
                355                 360                 365

Ser Asp Lys Asp Gly Tyr Lys His Ile His Tyr Ile Lys Asp Thr Val
            370                 375                 380

Glu Asn Ala Ile Gln Ile Thr Ser Gly Lys Trp Glu Ala Ile Asn Ile
385                 390                 395                 400

Phe Arg Val Thr Gln Asp Ser Leu Phe Tyr Ser Ser Asn Glu Phe Glu
                405                 410                 415

Asp Tyr Pro Gly Arg Arg Asn Ile Tyr Arg Ile Ser Ile Gly Ser Ser
                420                 425                 430

Pro Pro Ser Lys Lys Cys Ile Thr Cys His Leu Arg Lys Glu Arg Cys
                435                 440                 445

Gln Tyr Tyr Thr Ala Ser Phe Ser Asp Tyr Ala Lys Tyr Tyr Ala Leu
            450                 455                 460

Ile Cys Tyr Gly Pro Gly Leu Pro Ile Ser Thr Leu His Asp Gly His
465                 470                 475                 480

Thr Asp Gln Glu Ile Lys Ile Leu Glu Glu Asn Lys Glu Leu Glu Asn
                485                 490                 495

Ala Leu Lys Asn Ile Gln Leu Pro Lys Glu Ile Lys Lys Leu Glu
                500                 505                 510

Val Asp Asp Ile Thr Leu Trp Tyr Lys Met Met Leu Pro Pro Arg Phe
            515                 520                 525

Asp Arg Ser Lys Lys Tyr Pro Leu Leu Ile Gln Val Tyr Gly Gly Pro
            530                 535                 540

Cys Ser Gln Ser Val Lys Ser Val Phe Ser Ile Asn Trp Ile Ser Tyr
545                 550                 555                 560

Leu Ala Ser Lys Glu Gly Ile Val Ile Ala Leu Val Asp Gly Arg Gly
                565                 570                 575

Thr Ala Tyr Gln Gly Asp Lys Leu Leu Tyr Ala Val Tyr Arg Lys Leu
                580                 585                 590

Gly Val Tyr Glu Val Glu Asp Gln Ile Thr Ala Val Arg Lys Phe Ile
                595                 600                 605

Glu Met Gly Phe Ile Asp Glu Lys Arg Ile Ala Ile Trp Gly Trp Ser
            610                 615                 620

Tyr Gly Gly Tyr Val Ser Ser Leu Ala Leu Ala Ser Gly Thr Gly Leu
625                 630                 635                 640

Phe Lys Cys Gly Ile Ala Val Ala Pro Val Ser Ser Trp Glu Tyr Tyr
                645                 650                 655

Ala Ser Ile Tyr Thr Glu Arg Phe Met Gly Leu Pro Thr Lys Asn Asp
                660                 665                 670

Asn Leu Glu His Tyr Lys Asn Ser Thr Val Met Ala Arg Ala Glu Tyr
            675                 680                 685

Phe Arg Asn Val Asp Tyr Leu Leu Ile His Gly Thr Ala Asp Asp Asn
            690                 695                 700

Val His Phe Gln Asn Ser Ala Gln Ile Ala Lys Ala Leu Val Asn Ala
705                 710                 715                 720

Gln Val Asp Phe Gln Ala Met Trp Tyr Ser Asp Gln Asn His Gly Ile
                725                 730                 735
```

```
Pro Gly Leu Ser Ser Lys His Leu Tyr Thr Arg Met Thr His Phe Leu
            740                 745                 750
Lys Gln Cys Phe Ser Leu Ser Asp
        755                 760

<210> SEQ ID NO 40
<211> LENGTH: 30
<212> TYPE: DNA
<213> ORGANISM: Artificial Sequence
<220> FEATURE:
<223> OTHER INFORMATION: T127

<400> SEQUENCE: 40
ctttggagat actcttacac agcaacatat                                      30

<210> SEQ ID NO 41
<211> LENGTH: 30
<212> TYPE: DNA
<213> ORGANISM: Artificial Sequence
<220> FEATURE:
<223> OTHER INFORMATION: T127

<400> SEQUENCE: 41
ctttggagat actcttacac tgcaacatat                                      30

<210> SEQ ID NO 42
<211> LENGTH: 28
<212> TYPE: DNA
<213> ORGANISM: Artificial Sequence
<220> FEATURE:
<223> OTHER INFORMATION: A603

<400> SEQUENCE: 42
atcacagctg tcagaaaatt catagaaa                                        28

<210> SEQ ID NO 43
<211> LENGTH: 28
<212> TYPE: DNA
<213> ORGANISM: Artificial Sequence
<220> FEATURE:
<223> OTHER INFORMATION: A603

<400> SEQUENCE: 43
atcacagccg tcagaaaatt catagaaa                                        28
```

MONOCLONAL ANTIBODY AGAINST CANINE FIBROBLAST ACTIVATION PROTEIN THAT CROSS-REACTS WITH MOUSE AND HUMAN FIBROBLAST ACTIVATION PROTEIN (FAP)

CROSS-REFERENCE TO RELATED APPLICATION

The present application is entitled to priority under 35 U.S.C. § 119(e) to U.S. Provisional Patent Application No. 62/904,272 filed Sep. 23, 2019, which is hereby incorporated by reference in its entirety herein.

STATEMENT REGARDING FEDERALLY SPONSORED RESEARCH OR DEVELOPMENT

This invention was made with government support under CA172921 awarded by the National Institutes of Health. The government has certain rights in the invention.

REFERENCE TO AN ELECTRONIC SEQUENCE LISTING

The contents of the electronic sequence listing (File Name: 046483-7274US1 Sequence Listing.txt; Size: 26,721 bytes; and Date of Creation: Oct. 12, 2023) is incorporated herein by reference in its entirety.

BACKGROUND OF THE INVENTION

Tumors are composed of heterogeneous populations of cells, including transformed cells and a multitude of untransformed cells. Although the prevalence of different cell types varies among tumors and at different stages of tumor progression, they include infiltrating inflammatory and immune cells, endothelial cells, mesenchymal-derived smooth muscle cells, pericytes, and tumor-associated fibroblasts (TAFs), which are referred to herein collectively as stromal cells. TAFs are a heterogeneous population that can be phenotypically distinguished from normal fibroblasts. Fibroblast activation protein (FAP) has emerged as a marker of reactive fibroblasts in tumors as well as granulation tissue and in fibrotic lesions.

FAP is a type II transmembrane cell surface protein belonging to the post-proline dipeptidyl aminopeptidase family, sharing the highest similarity with dipeptidyl peptidase IV (DPPIV/CD26). FAP is expressed selectively by TAFs and pericytes in more than 90% of human epithelial cancers examined. It is also expressed during embryonic development, in tissues of healing wounds, and in chronic inflammatory and fibrotic conditions such as liver cirrhosis and idiopathic pulmonary fibrosis, as well as on bone and soft tissue sarcomas and some melanomas.

Expression of FAP is not however detected in benign lesions or normal adult tissues, while DPPIV is more widely expressed in a variety of cell types. In vitro studies have shown that FAP has both dipeptidyl peptidase and endopeptidase activity, including a collagenolytic activity capable of degrading gelatin and type I collagen, but it's in vivo substrate(s) is yet to be defined.

There is a need in the art for the development of antibodies that can cross-react with canine, mouse, and human fibroblast activation protein. The present invention addresses this need.

SUMMARY OF THE INVENTION

As described herein, the present invention relates to antibodies, binding polypeptides, and scFvs specific for fibroblast activation protein (FAP) capable of cross reacting with canine, mouse, and human FAP.

In one aspect, the invention provides an isolated binding polypeptide comprising an antigen-binding domain that specifically binds to an epitope of human and canine, and/or murine fibroblast activation protein (FAP).

In certain embodiments, the antigen-binding domain comprises a heavy chain variable region that comprises three heavy chain complementarity determining regions (HCDRs), wherein HCDR1 comprises the amino acid sequence YTITSYSLH (SEQ ID NO: 1), HCDR2 comprises the amino acid sequence EINPANGDHNFSEKFEIK (SEQ ID NO: 2), and HCDR3 comprises the amino acid sequence LDDSRFHWYFDV (SEQ ID NO: 3); and a light chain variable region that comprises three light chain complementarity determining regions (LCDRs), wherein LCDR1 comprises the amino acid sequence TASSSVSYMY (SEQ ID NO: 4), a LCDR2 comprises the amino acid sequence LTSNLA (SEQ ID NO: 5), and LCDR3 comprises the amino acid sequence QQWSGYPPIT (SEQ ID NO: 6).

In certain embodiments, the binding polypeptide: (a) binds a fibroblast activation protein (FAP); and/or (b) comprises an antibody or an antigen-binding fragment thereof, and/or (c) comprises a heavy chain variable region comprising an amino acid sequence having at least 80%, 85%, 90%, 95%, 96%, 96%, 97%, 98%, 99% identity to the amino acid sequence of the heavy chain variable region set forth in SEQ ID NO: 7; and/or (d) comprises a heavy chain variable region comprising an amino acid sequence set forth in SEQ ID NO: 7; and/or (e) consists of a heavy chain variable region consisting of an amino acid sequence set forth in SEQ ID NO: 7; and/or (f) comprises a light chain variable region comprising an amino acid sequence having at least 80%, 85%, 90%, 95%, 96%, 97%, 98%, 99% identity to the amino acid sequence set forth in SEQ ID NO: 9; and/or (g) comprises a light chain variable region comprising an amino acid sequence set forth in SEQ ID NO: 9; and/or (h) consists of a light chain variable region comprising an amino acid sequence set forth in SEQ ID NO: 9.

In certain embodiments, (a) the antigen-binding fragment is selected from the group consisting of a Fab, a single-chain variable fragment (scFv), or a single-domain antibody; and/or (b) the antigen-binding fragment is selected from the group consisting of a Fab, a single-chain variable fragment (scFv), or a single-domain antibody and wherein the antibody is a full-length antibody; and/or (c) the antigen-binding fragment is selected from the group consisting of a Fab, a single-chain variable fragment (scFv), or a single-domain antibody and wherein the antibody or antigen-binding fragment is a humanized antibody or an antigen-binding fragment thereof.

In certain embodiments, the binding polypeptide comprises a heavy chain variable region comprising the amino acid sequence set forth in SEQ ID NO: 7; and a light chain variable region comprising the amino acid sequence set forth in SEQ ID NO: 9.

In another aspect, the invention provides a single-chain variable fragment (scFv) comprising an antigen-binding domain that specifically binds to an epitope of human and canine, and/or murine fibroblast activation protein (FAP).

In certain embodiments, the antigen-binding domain comprises a heavy chain variable region that comprises three heavy chain complementarity determining regions (HCDRs), wherein HCDR1 comprises the amino acid sequence YTITSYSLH (SEQ ID NO: 1), HCDR2 comprises the amino acid sequence EINPANGDHNFSEKFEIK (SEQ ID NO: 2), and HCDR3 comprises the amino acid sequence LDDSRFHWYFDV (SEQ ID NO: 3); and a light chain variable region that comprises three light chain complementarity determining regions (LCDRs), wherein LCDR1 comprises the amino acid sequence TASSSVSYMY (SEQ ID NO: 4), a LCDR2 comprises the amino acid sequence LTSNLA (SEQ ID NO: 5), and LCDR3 comprises the amino acid sequence QQWSGYPPIT (SEQ ID NO: 6), wherein the heavy chain variable region and the light chain variable region are separated by a linker.

In certain embodiments, the single-chain variable fragment (scFv) comprises a heavy chain variable region comprising the amino acid sequence set forth in SEQ ID NO: 7; and a light chain variable region comprising the amino acid sequence set forth in SEQ ID NO: 9, wherein the heavy chain variable region and the light chain variable region are separated by a linker, and optionally wherein the linker comprises the amino acid sequence set forth in SEQ ID NO: 15.

In certain embodiments, the single chain variable fragment (scFv) comprises an amino acid sequence set forth in SEQ ID NOs: 11 or 13; or consists of an amino acid sequence set forth in SEQ ID NOs: 11 or 13.

In another aspect, the invention provides an isolated nucleic acid encoding any of the binding polypeptides contemplated herein.

In another aspect, the invention provides an isolated nucleic acid encoding a binding polypeptide comprising an antigen-binding domain that specifically binds an epitope of human and canine, and/or murine Fibroblast Activation Protein (FAP).

In certain embodiments, the antigen binding domain comprises a heavy chain variable region that comprises three heavy chain complementarity determining regions (HCDRs), wherein HCDR1 comprises the amino acid sequence YTITSYSLH (SEQ ID NO: 1), HCDR2 comprises the amino acid sequence EINPANGDHNFSEKFEIK (SEQ ID NO: 2), and HCDR3 comprises the amino acid sequence LDDSRFHWYFDV (SEQ ID NO: 3); and a light chain variable region that comprises three light chain complementarity determining regions (LCDRs), wherein LCDR1 comprises the amino acid sequence TASSSVSYMY (SEQ ID NO: 4), LCDR2 comprises the amino acid sequence LTSNLA (SEQ ID NO: 5), and LCDR3 comprises the amino acid sequence QQWSGYPPIT (SEQ ID NO: 6); and/or (b) the binding polypeptide comprises an antibody or an antigen-binding fragment thereof, and optionally wherein the antibody is a full-length antibody; and/or (c) the antigen-binding fragment is selected from the group consisting of a Fab, a single-chain variable fragment (scFv), or a single-domain antibody; and/or (d) the antibody or antigen-binding fragment is a humanized antibody or a fragment thereof.

In certain embodiments, (a) the heavy chain variable region is encoded by a nucleic acid comprising a polynucleotide sequence having at least 80%, 85%, 90%, 95%, 96%, 96%, 97%, 98%, 99% identity to SEQ ID NO: 8; and/or (b) the heavy chain variable region is encoded by a nucleic acid comprising the polynucleotide sequence set forth in SEQ ID NO: 8; and/or (c) the heavy chain variable region is encoded by a nucleic acid consisting of the polynucleotide sequence set forth in SEQ ID NO: 8; and/or (d) the light chain variable region is encoded by a nucleic acid comprising a polynucleotide sequence having at least 80%, 85%, 90%, 95%, 96%, 96%, 97%, 98%, 99% identity to the amino acid sequence of the light chain variable region set forth in SEQ ID NO: 10; and/or (e) the light chain variable region is encoded by a nucleic acid comprising the polynucleotide sequence set forth in SEQ ID NO: 10; and/or (f) the light chain variable region is encoded by a nucleic acid consisting of a polynucleotide sequence set forth in SEQ ID NO: 10.

In certain embodiments, the isolated nucleic acid comprises a heavy chain variable region encoded by a nucleic acid sequence comprising the polynucleotide sequence set forth in SEQ ID NO: 8; and a light chain variable region encoded by a nucleic acid sequence comprising the polynucleotide sequence set forth in SEQ ID NO: 10.

In certain embodiments, the nucleic acid (a) encodes a single-chain variable fragment (scFv) comprising a heavy chain variable region that comprises three heavy chain complementarity determining regions (HCDRs), wherein HCDR1 comprises the amino acid sequence YTITSYSLH (SEQ ID NO: 1), HCDR2 comprises the amino acid sequence EINPANGDHNFSEKFEIK (SEQ ID NO: 2), and HCDR3 comprises the amino acid sequence LDDSRFHWYFDV (SEQ ID NO: 3); and a light chain variable region that comprises three light chain complementarity determining regions (LCDRs), wherein LCDR1 comprises the amino acid sequence TASSSVSYMY (SEQ ID NO: 4), LCDR2 comprises the amino acid sequence LTSNLA (SEQ ID NO: 5), and LCDR3 comprises the amino acid sequence QQWSGYPPIT (SEQ ID NO: 6); or (b) encodes a single-chain variable fragment (scFv) comprising a heavy chain variable region comprising a nucleotide sequence set forth in SEQ ID NO: 8; and a light chain variable region comprising a nucleotide sequence set forth in SEQ ID NO: 10, wherein the heavy chain variable region and the light chain variable region are separated by a linker, and optionally wherein the linker comprises the amino acid sequence set forth in SEQ ID NO. 15; and/or (c) encodes a single-chain variable fragment (scFv) comprising a polynucleotide sequence set forth in SEQ ID NOs: 12 or 14; and/or (d) encodes a single-chain variable fragment (scFv) consisting of a polynucleotide sequence set forth in SEQ ID NOs: 12 or 14.

In another aspect, the invention provides a vector comprising any of the isolated nucleic acids contemplated herein.

In certain embodiments, the vector is an expression vector; and/or the vector is selected from the group consisting of a DNA vector, an RNA vector, a plasmid, a lentiviral vector, an adenoviral vector, an adeno-associated viral vector, and a retroviral vector.

In another aspect, the invention provides a host cell: (a) comprising any of the vectors contemplated herein; and/or (b) wherein the host cell is of eukaryotic or prokaryotic origin; and/or (c) wherein the host cell is of mammalian origin; and/or (d) wherein the host cell is of bacterial origin.

In another aspect, the invention provides a method of producing a binding polypeptide or scFv that binds to FAP. The method comprises culturing any of the host cells contemplated herein.

In another aspect, the invention provides a pharmaceutical composition comprising a binding polypeptidee comprising an antigen-binding domain that specifically binds to an epitope of human and canine, and/or murine fibroblast activation protein (FAP).

In another aspect, the invention provides a pharmaceutical composition comprising a single-chain variable fragment (scFv) comprising an antigen-binding domain that specifically binds to an epitope of human and canine, and/or murine fibroblast activation protein (FAP).

In another aspect, the invention provides a method for identifying a subject suitable for an adoptive cell therapy directed to Fibroblast Activation Protein (FAP). The method comprises: (a) isolating a diseased tissue from the subject;

(b) contacting the isolated tissue with a binding polypeptide that specifically binds FAP; and (c) detecting FAP-expressing cells in the isolated tissue, thereby identifying a suitable subject for the adoptive cell therapy.

In certain embodiments, the binding polypeptide comprises a heavy chain variable region that comprises three heavy chain complementarity determining regions (HCDRs), wherein HCDR1 comprises the amino acid sequence YTITSYSLH (SEQ ID NO: 1), HCDR2 comprises the amino acid sequence EINPANGDHNFSEKFEIK (SEQ ID NO: 2), and HCDR3 comprises the amino acid sequence LDDSRFHWYFDV (SEQ ID NO: 3); and a light chain variable region that comprises three light chain complementarity determining regions (LCDRs), wherein LCDR1 comprises the amino acid sequence TASSSVSYMY (SEQ ID NO: 4), a LCDR2 comprises the amino acid sequence LTSNLA (SEQ ID NO: 5), and LCDR3 comprises the amino acid sequence QQWSGYPPIT (SEQ ID NO: 6).

In certain embodiments, (a) the binding polypeptide comprises an antibody or an antigen-binding fragment thereof, and/or (b) the antigen-binding fragment is selected from the group consisting of a Fab, a single-chain variable fragment (scFv), or a single-domain antibody, and optionally wherein the antibody is a full-length antibody; and/or (c) the antibody or antigen-binding fragment is a humanized antibody or an antigen-binding fragment thereof, and/or (d) the binding polypeptide is conjugated to a therapeutic molecule or a diagnostic molecule; and/or (e) the binding polypeptide is conjugated to a diagnostic molecule, wherein the diagnostic molecule comprises a detectable label; and/or (f) the binding polypeptide is conjugated to a diagnostic molecule, wherein the diagnostic molecule comprises a detectable label, and further wherein the detectable label is a radiolabel, a fluorophore, an enzyme, a hapten, biotin, or a chromophore.

In certain embodiments, the subject is administered the adoptive cell therapy after the subject is identified as a suitable subject.

In certain embodiments, (a) the adoptive cell therapy comprises a modified immune cell comprising a chimeric antigen receptor (CAR); and/or (b) the adoptive cell therapy comprises a modified immune cell comprising a chimeric antigen receptor (CAR) and wherein the immune cells are T lymphocytes; and/or (c) the adoptive cell therapy comprises a modified immune cell comprising a chimeric antigen receptor (CAR) and wherein the immune cells are NK cells; and/or (d) the adoptive cell therapy comprises a modified immune cell comprising a chimeric antigen receptor (CAR), wherein the CAR specifically binds to FAP.

In certain embodiments, the binding polypeptide: (a) comprises a heavy chain variable region comprising an amino acid sequence having at least 80%, 85%, 90%, 95%, 96%, 96%, 97%, 98%, 99% identity to the amino acid sequence of the heavy chain variable region set forth in SEQ ID NO: 7; and/or (b) comprises a heavy chain variable region comprising an amino acid sequence set forth in SEQ ID NO: 7; and/or (c) consists a heavy chain variable region consisting of an amino acid sequence set forth in SEQ ID NO: 7; and/or (d) comprises a light chain variable region comprising an amino acid sequence having at least 80%, 85%, 90%, 95%, 96%, 97%, 98%, 99% identity to the amino acid sequence set forth in SEQ ID NO: 9; and/or (e) comprises a light chain variable region comprising an amino acid sequence set forth in SEQ ID NO: 9; and/or (f) consists of a light chain variable region comprising an amino acid sequence set forth in SEQ ID NO: 9.

In another aspect, the invention provides a method for treating a cancer in a subject in need thereof, comprising administering to the subject an isolated binding polypeptide comprising a heavy chain variable region comprising an amino acid sequence at least 80%, 85%, 90%, 95%, 96%, 97%, 98%, 99%, or 100% identical to SEQ ID NO: 7; and a light chain variable region comprising an amino acid sequence at least 80%, 85%, 90%, 95%, 96%, 97%, 98%, 99%, or 100% identical to SEQ ID NO: 9.

In certain embodiments, (a) the cancer is associated with fibroblast activation protein (FAP)-expressing cells; and/or (b) the FAP-expressing cell is a cancer-associated cell; and/or (c) the FAP-expressing cell is a cancer-associated cell, wherein the cancer-associated cell is a cancer-associated fibroblast (CAF); and/or (d) the FAP-expressing cell is a cancer-associated cell, wherein the FAP-expressing cancer-associated cell is a FAP-expressing adipocyte; and/or (e) the FAP-expressing cell is a cancer-associated cell, wherein the FAP-expressing cancer-associated cell is a tumor-associated macrophage (TAM); and/or (f) the FAP-expressing cell is a cancer-associated cell, wherein the FAP-expressing cancer-associated cell is a tumor-associated neutrophil (TAN); and/or (g) the FAP-expressing cell is a cancer-associated cell, wherein the FAP-expressing cancer-associated cell is a myeloid-derived suppressor cell (MDSC); and/or (h) the FAP-expressing cell is a cancer-associated cell, wherein the FAP-expressing cancer-associated cell is a cancer-initiating cell.

In certain embodiments, (a) the binding polypeptide specifically binds to fibroblast activation protein (FAP); and/or (b) the binding polypeptide comprises an antibody or an antigen-binding fragment thereof; and/or (c) the antigen-binding fragment is selected from the group consisting of a Fab, a single-chain variable fragment (scFv), or a single-domain antibody, and optionally wherein the antibody is a full-length antibody; and/or (d) the antibody or antigen-binding fragment is a humanized antibody or an antigen-binding fragment thereof.

In another aspect, the invention provides a method for treating cancer in a subject in need thereof, comprising: (a) identifying the subject as a suitable subject, wherein the identifying comprises: (i) isolating a diseased tissue from the subject; (ii) contacting the isolated tissue with a binding polypeptide that specifically binds FAP; and (iii) detecting FAP-expressing cells in the isolated tissue; and (b) administering to the suitable subject adoptive cell therapy comprising a modified T cell comprising a chimeric antigen receptor (CAR) that specifically binds to Fibroblast Activation Protein (FAP).

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1 shows sequence alignments between the amino acid sequence (SEQ ID NO; 39; Top) of a canine FAP encoded by the gene sequence listed in the NCBI database (XM_005640252.2) and the amino acid sequence of a FAP encoded by the product of the PCR amplification of the canine FAP gene (SEQ ID NO: 16) using two primers that were created using the NCBI sequence. At the nucleotide level, the PCR gene product (SEQ ID NO: 16) possessed two mutations at positions 381 (a to t) and 1809 (t to c) of SEQ ID NO: 16 (boxed residues in inset sequences, right). The top right inset discloses a sequence alignment between nucleotides 361-390 of SEQ ID NO: 16 (SEQ ID NO: 41) and SEQ ID NO: 40 (nucleotides 676 to 705 of XM_005640252.2). Bottom right inset discloses a sequence alignment between nucleotides 1799-1828 of SEQ ID NO: 16 (SEQ ID NO: 43) and SEQ ID NO: 42 (nucleotides 2116 to 2143 of XM_005640252.2). The mutations are conservative base-pair substitutions that do not affect the respective encoded threonine at position 127 (T127) or alanine at position 603 (A603) (boxed residues, left).

FIGS. 4A-4C illustrate the characterization of the isotype of the newly created 4G5 anti-canine FAP antibody. An ELISA-based commercial isotyping kit was used in these studies. FIG. 4A shows colorimetric data from the ELISA. Columns represent replicate wells of each row. Positive reactions are present in rows A and G. FIG. 4B is an image of the ELISA plate showing the significant positive signal in rows A and G. FIG. 4C is a plate map of the study showing that the 4G5 antibody tested positive for IgG1 and kappa isotype immunoglobulins.

DETAILED DESCRIPTION

A. Definitions

Figures 2A, 2B:
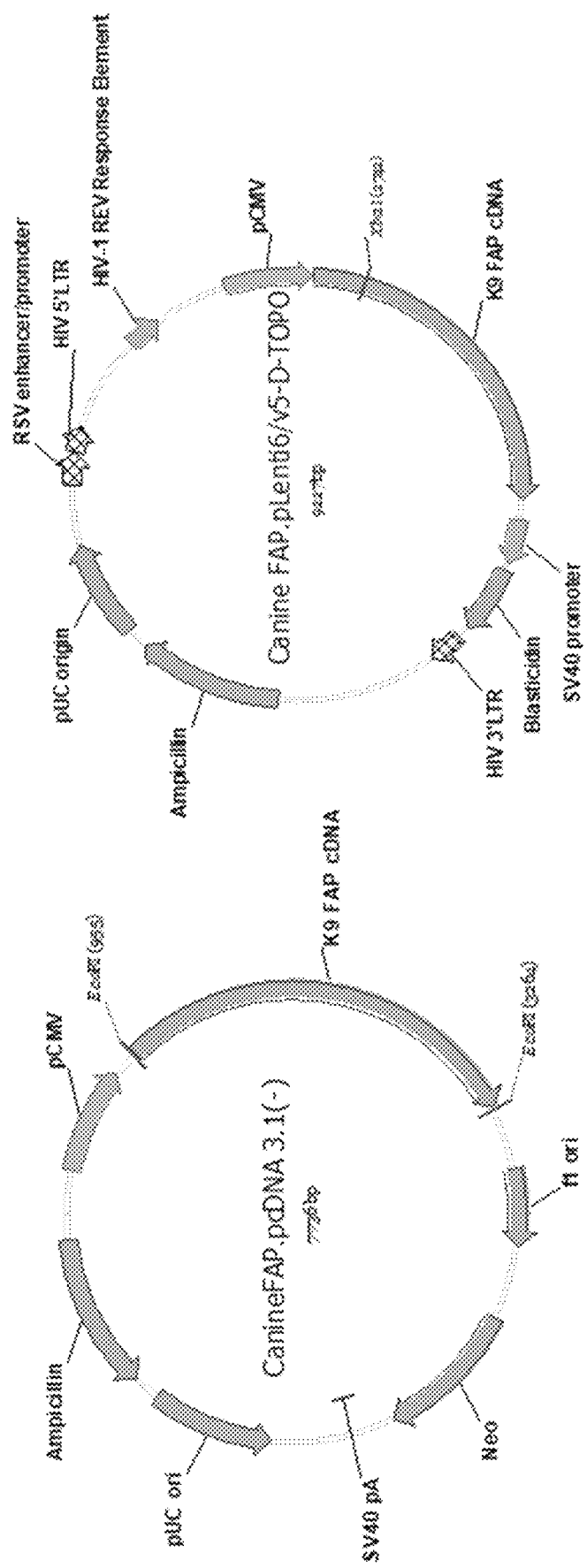
FIGS. 2A-2C are vector maps and a graph illustrating the creation of recombinant canine FAP-expressing cells. The canine FAP PCR product was cloned into a eukaryotic expression plasmid (pcDNA3.1) (FIG. 2A), and then subcloned into a lentiviral plasmid (pLenti6/v5-D-TOPO) (FIG. 2B). The lentiviral plasmid was transfected with packaging plasmids into HEK293 cells, which were used to generate virus-containing supernatant. The resulting viral particle-containing supernatant was used to transduce BALB/c 3T3 cells. Expression of recombinant canine FAP was confirmed by flow cytometry using a sheep anti-human FAP antibody (FIG. 2C).

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of 20% or ±10%, more preferably ±5%, even more preferably ±1%, and still more preferably ±0.1% from the specified value, as such variations are appropriate to perform the disclosed methods.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. Tetramers may be naturally occurring or reconstructed from single chain antibodies or antibody fragments. Antibodies also include dimers that may be naturally occurring or constructed from single chain antibodies or antibody fragments. The antibodies in the present invention may exist in a variety of forms including, for example, polyclonal antibodies, monoclonal antibodies, Fv, Fab and F(ab')$_2$, as well as single chain antibodies (scFv), humanized antibodies, and human antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')$_2$, and Fv fragments, linear antibodies, scFv antibodies, single-domain antibodies, such as camelid antibodies (Riechmann, 1999, Journal of Immunological Methods 231:25-38), composed of either a VL or a VH domain which exhibit sufficient affinity for the target, and multispecific antibodies formed from antibody fragments. The antibody fragment also includes a human antibody or a humanized antibody or a portion of a human antibody or a humanized antibody.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for the ability to bind FAP using the functional assays described herein.

"Co-stimulatory ligand", as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

The term "dysregulated" when used in the context of the level of expression or activity of FAP refers to the level of expression or activity that is different from the expression level or activity of FAP in an otherwise identical healthy animal, organism, tissue, cell or component thereof. The term "dysregulated" also refers to the altered regulation of the level of expression and activity of FAP compared to the regulation in an otherwise identical healthy animal, organism, tissue, cell or component thereof.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system.

Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" and "chimeric" forms of non-human (e.g., murine) antibodies are immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized and chimeric antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized and chimeric antibodies can comprise residues which are found neither in the recipient antibody nor in the imported CDR or framework sequences. These modifications are made to further refine and optimize antibody performance. In general, the humanized and chimeric antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized and chimeric antibody optimally also will comprise at least a portion of an immunoglobulin constant region (Fc), typically that of a human immunoglobulin. The World Health Organization (WHO) International Nonproprietary Name (INN) Expert Group has defined requirements for non-human derived antibodies to be considered "humanized". According to guidelines, comparison of a candidate antibody to human sequences should be done through the International Immunogenetics Information System® (IMGT®) DomainGapAlign tool (www.imgt.org). This tool interrogates the IMGT® database of antibody germline variable region genes where the alignment score is made only against germline sequence variable region exons, thus omitting part of CDR3 and the J region from the analysis. For an antibody to be "humanized", in addition to being "closer to human than to other species", the top "hit" should be human and the identity to human sequences must be at least 85%, otherwise the antibody would be designated as "chimeric". For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody, where the whole molecule is of human origin or consists of an amino acid sequence identical to a human form of the antibody.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the plasma membrane of a cell.

"Single chain antibodies" refer to antibodies formed by recombinant DNA techniques in which immunoglobulin heavy and light chain fragments are linked to each other using an engineered span of amino acids to recapitulate the Fv region of an antibody as a single polypeptide. Various methods of generating single chain antibodies are known, including those described in U.S. Pat. No. 4,694,778; Bird (1988) Science 242:423-442; Huston et al. (1988) Proc. Natl. Acad. Sci. USA 85:5879-5883; Ward et al. (1989) Nature 334:54454; Skerra et al. (1988) Science 242:1038-1041.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

By the term "specifically binds," as used herein, is meant an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell and/or on a tumor cell.

A "stimulatory ligand," as used herein, means a ligand that when present on an antigen presenting cell (e.g., an aAPC, a dendritic cell, a B-cell, and the like) or a tumor cell, can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

B. Binding Polypeptides, Antibodies, and scFvs

The binding polypeptides and antibodies of the invention are characterized by particular functional features or properties of the antibodies. In such embodiments, the antigen-binding domain may be referred to as cross-species reactive. For example, the binding polypeptides and antibodies specifically bind to canine fibroblast activation protein (FAP) and also cross-react to mouse and human FAP. Preferably, the binding polypeptides and antibodies of the invention bind to canine, mouse, and human FAP with high affinity. Preferably, the binding polypeptides and antibodies of the invention specifically recognize naturally expressed canine FAP protein on a cell and do not cross-react to other surface molecules on that cell.

In certain aspect, the invention provides an isolated binding polypeptide comprising an antigen-binding domain that specifically binds to an epitope of human and canine, and/or murine fibroblast activation protein (FAP). In certain embodiments, the antigen-binding domain comprises a heavy chain variable region that comprises three heavy chain complementarity determining regions (HCDRs) and a light chain variable region that comprises three light chain complementarity determining regions (LCDRs).

In certain embodiments, the invention provides an isolated binding polypeptide comprising a heavy chain variable region that comprises three heavy chain complementarity determining regions (HCDRs). In certain embodiments, HCDR1 comprises the amino acid sequence YTITSYSLH (SEQ ID NO: 1), and/or HCDR2 comprises the amino acid sequence EINPANGDHNFSEKFEIK (SEQ ID NO: 2), and/or HCDR3 comprises the amino acid sequence LDDSRFHWYFDV (SEQ ID NO: 3). In certain embodiments, the antigen-binding domain comprises a light chain variable region that comprises three light chain complementarity determining regions (LCDRs), wherein LCDR1 comprises the amino acid sequence TASSSVSYMY (SEQ ID NO: 4), and/or LCDR2 comprises the amino acid sequence LTSNLA (SEQ ID NO: 5), and/or LCDR3 comprises the amino acid sequence QQWSGYPPIT (SEQ ID NO: 6).

In certain aspect, the invention provides an isolated binding polypeptide comprising an HCDR1 comprising the amino acid sequence YTITSYSLH (SEQ ID NO: 1). Also provided is an isolated binding polypeptide comprising an HCDR1 comprising the amino acid sequence GYTITSYSLH (SEQ ID NO: 17). Also provided is an isolated binding polypeptide comprising an HCDR2 comprising the amino acid sequence EINPANGDHNFSEKFEIK (SEQ ID NO: 2). Also provided is an isolated binding polypeptide comprising an HCDR3 comprising the amino acid sequence LDDSRFHWYFDV (SEQ ID NO: 3). Also provided is an isolated binding polypeptide comprising an HCDR3 comprising the amino acid sequence TRLDDSRFHWYFDV (SEQ ID NO: 19). Also provided is an isolated binding polypeptide comprising a light chain variable region that comprises an LCDR1 comprising the amino acid sequence TASSSVSYMY (SEQ ID NO: 4). Also provided is an isolated binding polypeptide comprising an LCDR2 comprising the amino acid sequence LTSNLA (SEQ ID NO: 5). Also provided is an isolated binding polypeptide comprising an LCDR2 comprising the amino acid sequence LTSNLAS (SEQ ID NO: 20). Also provided is an isolated binding polypeptide comprising an LCDR3 comprising the amino acid sequence QQWSGYPPIT (SEQ ID NO: 6).

In certain embodiments, the invention provides an isolated binding polypeptide comprising a heavy chain variable region that comprises three heavy chain complementarity determining regions (HCDRs), wherein HCDR1 comprises the amino acid sequence YTITSYSLH (SEQ ID NO:1), and/or HCDR2 comprises the amino acid sequence EINPANGDHNFSEKFEIKAT (SEQ ID NO: 18), and/or HCDR3 comprises the amino acid sequence TRLDDSRFHWYFDV (SEQ ID NO: 19). In certain embodiments, the isolated binding polypeptide comprises a light chain variable region that comprises three light chain complementarity determining regions (LCDRs), wherein LCDR1 comprises the amino acid sequence TASSSVSYMY (SEQ ID NO: 4), and/or LCDR2 comprises the amino acid sequence LTSNLA (SEQ ID NO: 5), and/or LCDR3 comprises the amino acid sequence QQWSGYPPIT (SEQ ID NO: 6).

In certain aspect, the invention provides an isolated binding polypeptide comprising an HCDR1 comprising the amino acid sequence GYTITSYSLH (SEQ ID NO: 17), an HCDR2 comprising the amino acid sequence EINPANGDHNFSEKFEIK (SEQ ID NO: 2), an HCDR3 comprising the amino acid sequence LDDSRFHWYFDV (SEQ ID NO: 3), an LCDR1 comprising the amino acid sequence TASSSVSYMY (SEQ ID NO: 4), an LCDR2 comprising the amino acid sequence LTSNLAS (SEQ ID NO: 20), and an LCDR3 comprising the amino acid sequence QQWSGYPPIT (SEQ ID NO: 6).

In certain embodiments, the invention provides an isolated binding polypeptide comprising a heavy chain variable region that comprises any of the three heavy chain complementarity determining regions, HCDR1, HCDR2, and HCDR3, as described herein. In certain embodiments, the isolated binding polypeptide comprises a light chain variable region that comprises any of the three light chain complementarity determining regions, LCDR1, LCDR2, and LCDR3, as described herein. In certain embodiments, the isolated binding polypeptide comprises any combination of HCDR1, HCDR2, HCDR3, LCDR1, LCDR2, and LCDR3, as described herein. The skilled artisan would readily be able to determine the relevant complementarity determining regions based on amino acid numbering in view of the heavy and light chain variable region sequences provided herein.

Tolerable variations of the complementarity determining regions (CDR) sequences will be known to those of skill in the art. For example, in some embodiments the polypeptide comprises a complementarity determining region (HCDR or LCDR) that comprises an amino acid sequence that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any of the amino acid sequences set forth in SEQ ID NO: 1, 2, 3, 4, 5, 6, 17, 18, 19, or 20.

In some embodiments, the binding polypeptide binds a fibroblast activation protein (FAP). In some embodiments, the binding polypeptide comprises an antibody or an antigen-binding fragment thereof. In some embodiments, the antigen-binding fragment is selected from the group consisting of a Fab, a single-chain variable fragment (scFv), or a single-domain antibody. In further embodiments, the antibody is a full-length antibody. In yet further embodiments, the antibody or antigen-binding fragment is a mouse antibody or an antigen-binding fragment thereof. In some embodiments, the antibody or antigen-binding fragment is a humanized antibody or an antigen-binding fragment thereof.

In certain embodiments, the binding polypeptide comprises a heavy chain variable region comprising an amino acid sequence having at least 80%, 85%, 90%, 95%, 96%, 96%, 97%, 98%, or 99% identity to the amino acid sequence of the heavy chain variable region set forth in SEQ ID NO: 7. In certain embodiments, the binding polypeptide comprises a heavy chain variable region comprising an amino acid sequence set forth in SEQ ID NO: 7. In certain embodiments, the binding polypeptide consists of a heavy chain variable region consisting of an amino acid sequence set forth in SEQ ID NO: 7.

In certain embodiments, the binding polypeptide comprises a light chain variable region comprising an amino acid sequence having at least 80%, 85%, 90%, 95%, 96%, 97%, 98%, or 99% identity to the amino acid sequence set forth in SEQ ID NO: 9. In certain embodiments, the binding polypeptide comprises a light chain variable region comprising an amino acid sequence set forth in SEQ ID NO: 9. In certain embodiments, the binding polypeptide consists of a light chain variable region comprising an amino acid sequence set forth in SEQ ID NO: 9.

Also provided is an isolated binding polypeptide comprising a heavy chain variable region comprising the amino acid sequence set forth in SEQ ID NO: 7 and a light chain variable region comprising the amino acid sequence set forth in SEQ ID NO: 9.

In certain embodiments, the invention includes an antibody that binds to the same epitope on human, mouse, or canine FAP as an antibody of the invention (i.e., antibodies that have the ability to cross-compete for binding to canine FAP with any of the antibodies of the invention). In a preferred embodiment, the reference antibody for cross-competition studies can be one of the antibodies described herein (e.g., 4G5). For example, Biacore analysis, ELISA assays or flow cytometry may be used to demonstrate cross-competition with the antibodies of the current invention. The ability of a test antibody to inhibit the binding of, for example, 4G5, to canine FAP demonstrates that the test antibody can compete with 4G5 for binding to canine, mouse, and human FAP and thus is considered to bind to the same epitope of FAP as 4G5.

An antibody of the invention can be prepared using an antibody having one or more of the VH and/or VL sequences disclosed herein as a starting material to engineer a modified antibody, which modified antibody may have altered properties as compared with the starting antibody. An antibody can be engineered by modifying one or more amino acids within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

Also provided is a single-chain variable fragment (scFv) comprising an antigen-binding domain that specifically binds to an epitope of human and/or canine and/or murine fibroblast activation protein (FAP).

As used herein, the term "single-chain variable fragment" or "scFv" is a fusion protein of the variable regions of the heavy (VH) and light chains (VL) of an immunoglobulin (e.g., mouse or human) covalently linked to form a VH::VL heterodimer. The heavy (VH) and light chains (VL) are either joined directly or joined by a peptide-encoding linker, which connects the N-terminus of the VH with the C-terminus of the VL, or the C-terminus of the VH with the N-terminus of the VL. In some embodiments, the antigen binding domain (e.g., FAP binding domain) comprises an scFv having the configuration from N-terminus to C-terminus, VH-linker-VL. In some embodiments, the antigen binding domain comprises an scFv having the configuration from N-terminus to C-terminus, VL-linker-VH. Those of skill in the art would be able to select the appropriate configuration for use in the present invention.

The linker is usually rich in glycine for flexibility, as well as serine or threonine for solubility. The linker can link the heavy chain variable region and the light chain variable region of the extracellular antigen-binding domain. Non-limiting examples of linkers are disclosed in Shen et al., Anal. Chem. 80(6):1910-1917 (2008) and WO 2014/087010, the contents of which are hereby incorporated by reference in their entireties. Various linker sequences are known in the art, including, without limitation, glycine serine (GS) linkers such as (GS)$_n$, (GSGGS)$_n$ (SEQ ID NO:21), (GGGS)$_n$ (SEQ ID NO:22), and (GGGGS)$_n$ (SEQ ID NO:23), where n represents an integer of at least 1. Exemplary linker sequences can comprise amino acid sequences including, without limitation, GGSG (SEQ ID NO:24), GGSGG (SEQ ID NO:25), GSGSG (SEQ ID NO:26), GSGGG (SEQ ID NO:27), GGGSG (SEQ ID NO:28), GSSSG (SEQ ID NO:29), GGGGS (SEQ ID NO:30), GGGGSGGGGSGGGGS (SEQ ID NO:15) and the like. Those of skill in the art would be able to select the appropriate linker sequence for use in the present invention. In one embodiment, an scFv of the present invention comprises a heavy chain variable region (VH) and a light chain variable region (VL), wherein the VH and VL is separated by the linker sequence having the amino acid sequence GGGGSGGGGSGGGGS (SEQ ID NO:15), which may be encoded by the nucleic acid sequence GGTGGCGGTGGCTCGGGCGGTGGT GGGTCGGGTGGCGGCGGATCT (SEQ ID NO:31).

Despite removal of the constant regions and the introduction of a linker, scFv proteins retain the specificity of the original immunoglobulin. Single chain Fv polypeptide antibodies can be expressed from a nucleic acid comprising VH- and VL-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hyrbidoma (Larchmt) 2008 27(6):455-51; Peter et al., J Cachexia Sarcopenia Muscle 2012 Aug. 12; Shieh et al., J Imunol 2009 183(4):2277-85; Giomarelli et al., Thromb Haemost 2007 97(6):955-63; Fife et al., J Clin Invst 2006 116(8):2252-61; Brocks et al., Immunotechnology 1997 3(3):173-84; Moosmayer et al., Ther Immunol 1995 2(10:31-40). Agonistic scFvs having stimulatory activity have been described (see, e.g., Peter et al., J Bioi Chem 2003 25278(38):36740-7; Xie et al., Nat Biotech 1997 15(8):768-71; Ledbetter et al., Crit Rev Immunol 1997 17(5-6):427-55; Ho et al., BioChim Biophys Acta 2003 1638(3):257-66).

In certain aspect, the invention provides a single-chain variable fragment (scFv) comprising an antigen-binding domain that specifically binds to an epitope of human and canine, and/or murine fibroblast activation protein (FAP), wherein the antigen-binding domain comprises a heavy chain variable region that comprises three heavy chain complementarity determining regions (HCDRs) and a light chain variable region that comprises three light chain complementarity determining regions (LCDRs).

In certain embodiments of the scFv, HCDR1 comprises the amino acid sequence YTITSYSLH (SEQ ID NO: 1), and/or HCDR2 comprises the amino acid sequence EIN-PANGDHNFSEKFEIK (SEQ ID NO: 2), and/or HCDR3 comprises the amino acid sequence LDDSRFHWYFDV (SEQ ID NO: 3) and/or LCDR1 comprises the amino acid sequence TASSSVSYMY (SEQ ID NO: 4), and/or LCDR2 comprises the amino acid sequence LTSNLA (SEQ ID NO: 5), and/or LCDR3 comprises the amino acid sequence QQWSGYPPIT (SEQ ID NO: 6). The heavy chain variable region and the light chain variable region are separated by a linker.

In certain embodiments of the scFv, HCDR1 comprises the amino acid sequence GYTITSYSLH (SEQ ID NO: 17), and/or HCDR2 comprises the amino acid sequence EIN-PANGDHNFSEKFEIK (SEQ ID NO: 2), and/or HCDR3 comprises the amino acid sequence LDDSRFHWYFDV (SEQ ID NO: 3) and/or LCDR1 comprises the amino acid sequence TASSSVSYMY (SEQ ID NO: 4), and/or LCDR2 comprises the amino acid sequence LTSNLAS (SEQ ID NO: 20), and/or LCDR3 comprises the amino acid sequence QQWSGYPPIT (SEQ ID NO: 6). The heavy chain variable region and the light chain variable region are separated by a linker.

Also provided is a single-chain variable fragment (scFv) comprising a heavy chain variable region comprising the amino acid sequence set forth in SEQ ID NO: 7 and/or a light chain variable region comprising the amino acid sequence set forth in SEQ ID NO: 9. The heavy chain variable region and the light chain variable region are separated by a linker.

In another aspect, a single chain variable fragment (scFv) comprising an amino acid sequence set forth in SEQ ID NOs: 11 or 13, is provided. In another aspect, a single chain variable fragment (scFv) consisting of an amino acid sequence set forth in SEQ ID NOs: 11 or 13, is provided.

Tolerable variations of the scFv sequences will be known to those of skill in the art. For example, in some embodiments the scFv comprises an amino acid sequence that has at least 80%, at least 81%, at least 82%, at least 83%, at least 84%, at least 85%, at least 86%, at least 8700, at least 88%, at least 89%, at least 90%, at least 91%, at least 92%, at least 9300, at least 94%, at least 9500 at least 9600, at least 9700 at least 9800, or at least 9900 sequence identity to any of the amino acid sequences set forth in SEQ ID NO: 1, 2, 3, 4, 5, 6, 7, 9, 11, 13, 15, 17, 18, 19, or 20.

TABLE 1

Amino Acid and Nucleotide Sequences

| SEQ ID NO: | Name | Amino Acid/Nucleotide Sequence |
|---|---|---|
| 1 | 4G5 HCDR1 | YTITSYSLH |
| 2 | 4G5 HCDR2 | EINPANGDHNFSEKFEIK |
| 3 | 4G5 HCDR3 | LDDSRFHWYFDV |
| 4 | 4G5 LCDR1 | TASSSVSYMY |

TABLE 1-continued

Amino Acid and Nucleotide Sequences

| SEQ ID NO: | Name | Amino Acid/Nucleotide Sequence |
|---|---|---|
| 5 | 4G5 LCDR2 | LTSNLA |
| 6 | 4G5 LCDR3 | QQWSGYPPIT |
| 7 | 4G5 VH | QVQLQQPGAELVKPGASVKLSCKASGYTITSYSLHWVKQRPGQGL<br>EWIGEINPANGDFINFSEKFEIKATLTVDSSSNTAFMQLSRLTSE<br>DSAVYYCTRLDDSRFHWYFDVWGAGTTVTVSS |
| 8 | 4G5 VH | CAGGTCCAACTGCAGCAGCCTGGGGCTGAACTGGTAAAGCCTGGG<br>GCCTTCAGTGAAGTTGTCCTGCAAGGCGTCTGGCTACACCATCAC<br>CAGCTACTCTCTGCACTGGGTGAAGCAGAGGCCTGGACAAGGCCT<br>TGAGTGGATTGGAGAGATTAATCCTGCCAATGGTGATCATAACTT<br>CAGTGAGAAGITCGAGATCAAGGCCACACTGACTGTAGACAGCTC<br>CTCCAACACAGCATTCATGCAACTCAGCAGGCTGACATCTGAGGA<br>CTCTGCGGTCTATTACTGTACAAGATTGGACGATAGTAGGTTCCA<br>CTGGTACFICGATGTCTGGGGCGCAGGGACCACGGTCACCGTCTC<br>CTCA |
| 9 | 4G5 VL | QIVLTQSPALMSASPGEKVTMTCTASSSVSYMYWYQQKPRSSPKP<br>WIFLTSNLASGVPARFSGRGSGTSFSLTISSMEAEDAATYYCQQW<br>SGYPPITFGSGTKLE1K |
| 10 | 4G5 VL | CAAATTGTTCTCACCCAGTCTCCAGCGCTCATGTCTGCTTCTCCA<br>GGGGAGAAGGTCACCATGACCTGCACTGCCAGCTCAAGTGTTAGT<br>TACNTGTACTGGTACCAGCAGAAGCCACGATCCTCCCCCAAACCC<br>TGGATTTTTCTCACCTCCAACCTGGCTTCTGGAGTCCCTGCTCGC<br>TTCAGTGGCCGTGGGTCTGGGACCTCTTTCTCTCTCACAATCAGC<br>AGCATGGAGGCTGAAGATGCTGCCACTTATTACTGCCAGCAGTGG<br>AGTGGTTACCCACCCATCACATTCGGCTCGGGGACAAAGTTGGAA<br>ATAAAA |
| 11 | 4G5 scFv<br>(VL > VH) | QIVLTQSPALMSASPGEKVTMTCTASSSVSITYMVYQQKPRSSPK<br>PWIFLTSNLASGVPARFSGRGSGTSFSLTISSMEAEDAATYYCQQ<br>WSGYPPITFGSGTKLEIKGGGGSGGGGSGGGGSQVQLQQPGAELV<br>KPGASVKLSCKASGYTITSYSLHWVKQRPGQGLEWIGEINPANGD<br>HNFSEKFEIKATLTVDSSSNTAFMQLSRLTSEDSAVYYCTRLDDS<br>RFHWYFDVWGAGTTVTVSS |
| 12 | 4G5 scFv<br>(VL > VH) | CAAATTGTTCTCACCCAGTCTCCAGCGCTCATGTCTGCTTCTCCA<br>GGGGAGAAGGTCACCATGACCTGCACTGCCAGCTCAAGTGTTAGT<br>TACATGTACTGGTACCAGCAGAAGCCACGATCCTCCCCCAAACCC<br>TGGATTTTTCTCACCTCCAACCTGGCTTCTGGAGTCCCTGCTCGC<br>TTCAGTGGCCGTGGGTCTGGGACCTCTTTCTCTCTCACAATCAGC<br>AGCATGGAGGCTGAAGATGCTGCCACTTATTACTGCCAGCAGTGG<br>AGTGGTTACCCACCCATCACATTCGGCTCGGGGACAAAGTTGGAA<br>ATAAAAGGTGGAGGTGGCAGCGGAGGAGGTGGGTCCGGCGGTGGA<br>GGAAGCCAGGTCCAACTGCAGCAGCCTGGGGCTGAACTGGTAAAG<br>CCTGGGGcTTCAGTGAAGTTGTCCTGCAAGGCGTCTGGCTACACC<br>ATCACCAGCTACTCTCTGCACTGGGTGAAGCAGAGGCCTGGACAA<br>GGCCTTGAGTGGATTGGAGAGATTAATCCTGCCAATGGTGATCAT<br>AACTTCAGTGAGAAGTTCGAGATCAAGGCCACACTGACTGTAGAC<br>AGCTCCTCCAACACAGCATTCATGCAACTCAGCAGGCTGACATCT<br>GAGGACTCTGCGGTCTATTACTGTACAAGATTGGACGATAGTAGG<br>TTCCACTGGTACTTCGATGTCTGGGCGCAGGGACCACGGTCACC<br>GTCTCCTCA |
| 13 | 4G5 scFv<br>(VH > VL) | QVQLQQPGAELVKPGASVKLSCKASGYTITSYSLHWVKQRPGQGL<br>EWIGEINPANGDHNFSEKFEIKATLIVDSSSNTAFMQLSRLTSED<br>SAVYYCTRLDDSRFHWYFIWWGAGTIVTVSSGGGGSGGGGSGGGG<br>SQIVLTQSPALMSASPGEKVIMTCTASSSVSYMYWYQQKPRSSPK<br>PWIFLTSNLASGVPARFSGRGSGTSFSLTISSMEAEDAATYYCQQ<br>WSGYPPITFGSGTKLEIK |
| 14 | 4G5 scFv<br>(VH > VL) | CAGGTCCAACTGCAGCAGCCTGGGGCTGAACTGGTAAAGCCTGGG<br>GCTTCAGTGAAGTTGTCCTGCAAGGCGTCTGGCTACACCATCACC<br>AGCTACTCTCTGCACTGGGTGAAGCAGAGGCCTGGACAAGGCCTT<br>GAGTGGATTGGAGAGATTAATCCTGCCAATGGTGATCATAACTTC<br>AGTGAGAAGTTCGAGATCAAGGCCACACTGACTGTAGACAGCTCC<br>TCCAACACAGCATTCATGCAACTCAGCAGGCTGACATCTGAGGAC<br>TCTGCGGTCTATTACTGTACAAGATTGGACGATAGTAGGTTCCAC<br>TGGTACTTCGATGTCTGGGCGCAGGGACCACGGTCACCGTCTCC<br>TCAGGTGGAGGTGGCAGCGGAGGAGGTGGGTCCGGCGGTGGAGGA<br>AGCCAAATTGTTCTCACCCAGTCTCCAGCGCTCATGTCTGCTTCT<br>CCAGGGGAGAAGGTCACCATGACCTGCACTGCCAGCTCAAGTGTT |

TABLE 1-continued

Amino Acid and Nucleotide Sequences

| SEQ ID NO: | Name | Amino Acid/Nucleotide Sequence |
|---|---|---|
| | | AGTTACATGTACTGGTACCAGCAGAAGCCACGATCCTCCCCCAAA<br>CCCTGGATTTTTCTCACCTCCAACCTGGCTTCTGGAGTCCCTGCT<br>CGCTTCAGTGGCCGTGGGTCTGGGACCTCTTTCTCTCTCACAATC<br>AGCAGCATGGAGGCTGAAGATGCTGCCACTTATTACTGCCAGCAG<br>TGGAGTGGTTACCCACCCATCACATTCGGCTCGGGGACAAAGTTG<br>GAAATAAAA |
| 15 | linker | GGGGSGGGGSGGGGS |
| 16 | Full Length Canine FAP | ATGAAGACGTGGTTAAAAATTGTATTTGGAGTTGCCACCTCTGCT<br>GTGCTTGCTTTATEGGTGATGTGCATTGTCTTACGTCCTTCAAGA<br>GTTCATGACTCCGAAGGAGGTACAACAAGAGCACTCACACTGGAG<br>GATATTTTAAATGGGACATTTACCTATAAAACATTTTTTCCAAAC<br>TGGATTTCAGGACAAGAATATCTTCATCAGTCTACAGATAATGAT<br>ATAGTATATTACAATATTGAAACAGGAGAATCATATACCATTTTG<br>AGTAATGCCACCATGAAAAGTGTGAATGCTTCAAATTATGGCTTA<br>TCACCTGATCGTCAATTTGCATATCTAGAAAGTGATTATTCAAAG<br>CTTTGGAGATACTCTTACACTGCAACATATCACATCTATAACCTC<br>AATAATGGAGAGTTTATAAGAAGAAATGAGCTTCCTCGTCCAATT<br>CAGTATTTATGCTGGTCGCCTGTTGGGAGTAAATTAGCATATGTC<br>TATCAAAACAATATCTATTTGAAACAAAGACCAGAAGACCCACCT<br>TTTTCAAATAACATATAATGGAAGAGAAAATAAAATATTCAATGG<br>AATCCCAGACTGGGTATATGAAGAGGAAATGCTTGCTACAAAACA<br>TGCTCTCTGGTGGTCTCCTAATGGAAAATTTTTGGCATATGCAGA<br>ATTTAATGATACAGAGATACCAGTTATTGCCTATTCCTATTATGG<br>TGATGAACAATATCCTAGAACAATAAATATTCCATACCCAAAGGC<br>TGGAGCTAAGAACCCTGTTGTTCGGATCTTTATTATCGATACCAC<br>TTATCCTCAGCAGACAGGTCCCAGAGAAGTGCCAGTTCCAGCAAT<br>GATAGCATCAAGTGATTATTATTTCAGTTGGCTCACATGGGTTAC<br>TGATGAACGAGTATGTTTGCAGTGGCTAAAAAGAATCCAGAACGT<br>TTCAGTTCTGTCCATATGTGATTTCAGGGAAGGCTGGCAGACATG<br>GGATTGTCCAAAGGCCCAGGAACATATAGAAGAAAGCAGAACTGG<br>ATGGGCTGGTGGATTCTTTGTTTCAACACCAGTTTrCAGCTATGA<br>TGCCATTTCATACTACAAAATATTTAGCGACAAGGATGGCTACAA<br>ACATATTCACTATATCAAAGACACTGTGGAAAATGCTATTCAAAT<br>TACAAGTGGCAAGTGGGAGGCCATAAATATATTCAGAGTAACACA<br>GGATTCACTGTTTTATTCTAGCAATGAATTTGAAGACTACCCAGG<br>AAGAAGAAATATCTATAGAATTAGCATTGGAAGCTCTCCTCCAAG<br>CAAAAAGTGCATTACTTGCCATCTAAGGAAAGAAAGGTGCCAATA<br>TTACACAGCAAGTTTCAGTGACTACGCCAAGTACTATGCACTTAT<br>CTGCTATGGCCCAGGCCTCCCCATTTCCACCCTTCATGACGGCCA<br>CACTGATCAAGAAATTAAAATCCTGGAAGAAAACAAAGAATTGGA<br>AAATGCTTTGAAAAAATATCCAGCTGCCTAAAGAGGAAATTAAGAA<br>ACTTGAAGTGGATGATATTACTTTATGGTACAAGATGATGCTTCC<br>TCCCCGGTTTGACAGATCAAAGAAGTATCCCTTGCTAATTCAAGT<br>GTATGGTGGTCCCTGCAGTCAGAGCGTAAAGTCTGTATTCAGTAT<br>TAATTGGATTTCTTATCTTGCAAGTAAGGAAGGGATAGTCATTGC<br>CTTGGTGGATGGCCGAGGAACAGCTTACCAAGGTGACAAACTCCT<br>GTATGCAGTATATCGAAAGCTGGGTGTTTATGAAGTTGAGGACCA<br>GATCACAGCCGTCAGAAAATTVATAGAAATGGGTTTCATTGATGA<br>AAAAAGAATAGCCATATGGGGCTGGTCCTATGGAGGCTATGTTTC<br>ATCACTGGCCCTTGCTTCAGGAACTGGTCTTTTCAAATGTGGGAT<br>AGCAGTGGCTCCTGTCTCCAGCTGGGAATATTACGCATCTATCTA<br>CACAGAACGATTCATGGGCCTCCCAACAAAGAACGATAATCTCGA<br>GCACTACAAAAATMAACTGTGATGGCAAGAGCAGAATATTTCAGA<br>AATGTAGACTATCTTCTCATCCACGGAACAGCAGATGATAATGTG<br>CACTTTCAAAACTCAGCACAGATTGCTAAAGCTCTGGTTAATGCA<br>CAAGTGGATTTCCAGGCAATGTGGTACTCTGACCAGAACCATGGC<br>ATACCCGGCCTGTCCTCGAAGCACTTATATACCCGCATGACCCAC<br>TTCCTAAAGCAGTGTTTTCTTTGTCCGACTGA |
| 17 | 4G5 HCDR1 | GYTITSYSLH |
| 18 | 4G5 HCDR2 | EINPANGDHNFSEKFEIKAT |
| 19 | 4G5 HCDR3 | TRLDDSRFHWYFDV |
| 20 | 4G5 LCDR2 | LTSNLAS |

C. Nucleic Acids and Expression Vectors

The present disclosure provides an isolated nucleic acid encoding a binding polypeptide (e.g. an antibody or fragment thereof, e.g. scFv) comprising an antigen-binding domain that specifically binds an epitope of human and canine, and/or murine Fibroblast Activation Protein (FAP). The nucleic acid of the present disclosure may comprise a polynucleotide sequence encoding any one of the binding polypeptides, scFvs, or antibodies disclosed herein.

In certain embodiments, the binding polypeptide comprises an antigen binding domain comprising a heavy chain variable region that comprises three heavy chain complementarity determining regions (HCDRs), wherein HCDR1 comprises the amino acid sequence YTITSYSLH (SEQ ID NO: 1), and/or HCDR2 comprises the amino acid sequence EINPANGDHNFSEKFEIK (SEQ ID NO: 2), and/or HCDR3 comprises the amino acid sequence LDDSRFHWYFDV (SEQ ID NO: 3). In certain embodiments, the antigen-binding domain also comprises a light chain variable region that comprises three light chain complementarity determining regions (LCDRs), wherein LCDR1 comprises the amino acid sequence TASSSVSYMY (SEQ ID NO: 4), and/or LCDR2 comprises the amino acid sequence LTSNLA (SEQ ID NO: 5), and/or LCDR3 comprises the amino acid sequence QQWSGYPPIT (SEQ ID NO: 6).

In certain embodiments, the binding polypeptide comprises an antigen binding domain comprising a heavy chain variable region wherein HCDR1 comprises the amino acid sequence GYTITSYSLH (SEQ ID NO: 17), and/or HCDR2 comprises the amino acid sequence EINPANGDHNFSEKFEIK (SEQ ID NO: 2), and/or HCDR3 comprises the amino acid sequence LDDSRFHWYFDV (SEQ ID NO: 3); and/or a light chain variable region wherein LCDR1 comprises the amino acid sequence TASSSVSYMY (SEQ ID NO: 4), and/or LCDR2 comprises the amino acid sequence LTSNLAS (SEQ ID NO: 20), and/or LCDR3 comprises the amino acid sequence QQWSGYPPIT (SEQ ID NO: 6).

In certain embodiments, the binding polypeptide comprises an antigen binding domain comprising a heavy chain variable region wherein HCDR1 comprises the amino acid sequence YTITSYSLH (SEQ ID NO: 1), and/or HCDR2 comprises the amino acid sequence EINPANGDHNFSEKFEIKAT (SEQ ID NO: 18), and/or HCDR3 comprises the amino acid sequence TRLDDSRFHWYFDV (SEQ ID NO: 19); and/or a light chain variable wherein LCDR1 comprises the amino acid sequence TASSSVSYMY (SEQ ID NO: 4), and/or LCDR2 comprises the amino acid sequence LTSNLA (SEQ ID NO: 5), and/or LCDR3 comprises the amino acid sequence QQWSGYPPIT (SEQ ID NO: 6).

In certain embodiments, the nucleic acid encoding the binding polypeptide comprises an antigen-binding domain comprising a heavy chain variable region that comprises any of the three heavy chain complementarity determining regions, HCDR1, HCDR2, and HCDR3, as described herein. In certain embodiments, the antigen-binding domain comprises a light chain variable region that comprises any of the three light chain complementarity determining regions, LCDR1, LCDR2, and LCDR3, as described herein. In certain embodiments, the antigen-binding domain comprises any combination of HCDR1, HCDR2, HCDR3, LCDR1, LCDR2, and LCDR3, and described herein. The skilled artisan would readily be able to determine the relevant complementarity determining regions based on amino acid numbering in view of the heavy and light chain variable region sequences provided herein.

In certain embodiments, the binding polypeptide comprises an antibody or an antigen-binding fragment thereof. In certain embodiments, the antigen-binding fragment is selected from the group consisting of a Fab, a single-chain variable fragment (scFv), or a single-domain antibody. In certain embodiments, the antibody is a full-length antibody. In certain embodiments, the antibody or antigen-binding fragment is a humanized antibody or a fragment thereof.

Also provide is a nucleic acid encoding a binding polypeptide comprising an antigen-binding domain that specifically binds an epitope of human and canine, and/or murine Fibroblast Activation Protein (FAP), wherein the heavy chain variable region is encoded by a nucleic acid comprising a polynucleotide sequence having at least 80%, 85%, 90%, 95%, 96%, 96%, 97%, 98%, 99% identity to SEQ ID NO: 8. In certain embodiments, the heavy chain variable region is encoded by a nucleic acid comprising the polynucleotide sequence set forth in SEQ ID NO: 8. In certain embodiments, the heavy chain variable region is encoded by a nucleic acid consisting of the polynucleotide sequence set forth in SEQ ID NO: 8.

In certain embodiments, the light chain variable region is encoded by a nucleic acid comprising a polynucleotide sequence having at least 80%, 85%, 90%, 95%, 96%, 96%, 97%, 98%, 99% identity to the amino acid sequence of the light chain variable region set forth in SEQ ID NO: 10. In certain embodiments, the light chain variable region is encoded by a nucleic acid comprising the polynucleotide sequence set forth in SEQ ID NO: 10. In certain embodiments, the light chain variable region is encoded by a nucleic acid consisting of a polynucleotide sequence set forth in SEQ ID NO: 10.

Also provided is an isolated nucleic acid encoding a binding polypeptide comprising a heavy chain variable region encoded by a nucleic acid sequence comprising the polynucleotide sequence set forth in SEQ ID NO: 8, and a light chain variable region encoded by a nucleic acid sequence comprising the polynucleotide sequence set forth in SEQ ID NO: 10.

Also provided is an isolated nucleic acid encoding a single-chain variable fragment (scFv) comprising a heavy chain variable region that comprises three heavy chain complementarity determining regions (HCDRs) and a light chain variable region that comprises three light chain complementarity determining regions (LCDRs). In certain embodiments, HCDR1 comprises the amino acid sequence GYTITSYSLH (SEQ ID NO: 17), and/or HCDR2 comprises the amino acid sequence EINPANGDHNFSEKFEIK (SEQ ID NO: 2), and/or HCDR3 comprises the amino acid sequence LDDSRFHWYFDV (SEQ ID NO: 3), and/or LCDR1 comprises the amino acid sequence TASSSVSYMY (SEQ ID NO: 4), and/or LCDR2 comprises the amino acid sequence LTSNLAS (SEQ ID NO: 20), and/or LCDR3 comprises the amino acid sequence QQWSGYPPIT (SEQ ID NO: 6).

In certain embodiments, the nucleic acid encodes a single-chain variable fragment that comprises a heavy chain variable region that comprises three heavy chain complementarity determining regions (HCDRs), wherein HCDR1 comprises the amino acid sequence YTITSYSLH (SEQ ID NO: 1), and/or HCDR2 comprises the amino acid sequence EINPANGDHNFSEKFEIK (SEQ ID NO: 2), and/or HCDR3 comprises the amino acid sequence LDDSRFHWYFDV (SEQ ID NO: 3). In certain embodiments, the light chain variable region comprises three light chain complementarity determining regions (LCDRs), wherein LCDR1 comprises the amino acid sequence TASSSVSYMY (SEQ ID NO: 4), and/or LCDR2 comprises the amino acid sequence LTSNLA (SEQ ID NO: 5), and/or LCDR3 comprises the amino acid sequence QQWSGYPPIT (SEQ ID NO: 6).

In certain embodiments, the nucleic acid comprises a single-chain variable fragment comprising a heavy chain variable region that comprises three heavy chain complementarity determining regions (HCDRs), wherein HCDR1 comprises the amino acid sequence GYTITSYSLH (SEQ ID NO: 17), and/or HCDR2 comprises the amino acid sequence EINPANGDHNFSEKFEIK (SEQ ID NO: 2), and/or HCDR3 comprises the amino acid sequence LDDSRFHWYFDV (SEQ ID NO: 3). In certain embodiments, the antigen-binding domain comprises a light chain variable region that comprises three light chain complementarity determining regions (LCDRs), wherein LCDR1 comprises the amino acid sequence TASSSVSYMY (SEQ ID NO: 4), and/or LCDR2 comprises the amino acid sequence LTSNLAS (SEQ ID NO: 20), and/or LCDR3 comprises the amino acid sequence QQWSGYPPIT (SEQ ID NO: 6).

In certain embodiments, the nucleic acid comprises a single-chain variable fragment comprising a heavy chain variable region that comprises three heavy chain complementarity determining regions (HCDRs), wherein HCDR1 comprises the amino acid sequence YTITSYSLH (SEQ ID NO: 1), and/or HCDR2 comprises the amino acid sequence EINPANGDHNFSEKFEIKAT (SEQ ID NO: 18), and/or HCDR3 comprises the amino acid sequence TRLDDSRFHWYFDV (SEQ ID NO: 19). In certain embodiments, the single-chain variable fragment also comprises a light chain variable region that comprises three light chain complementarity determining regions (LCDRs), wherein LCDR1 comprises the amino acid sequence TASSSVSYMY (SEQ ID NO: 4), and/or LCDR2 comprises the amino acid sequence LTSNLA (SEQ ID NO: 5), and/or LCDR3 comprises the amino acid sequence QQWSGYPPIT (SEQ ID NO: 6).

In certain embodiments, the nucleic acid comprising the single-chain variable fragment comprises a heavy chain variable region that comprises any of the three heavy chain complementarity determining regions, HCDR1, HCDR2, and HCDR3, as described herein. In certain embodiments, the single-chain variable fragment comprises a light chain variable region that comprises any of the three light chain complementarity determining regions, LCDR1, LCDR2, and LCDR3, as described herein. In certain embodiments, the single-chain variable fragment comprises any combination of HCDR1, HCDR2, HCDR3, LCDR1, LCDR2, and LCDR3, and described herein. The skilled artisan would readily be able to determine the relevant complementarity determining regions based on amino acid numbering in view of the heavy and light chain variable region sequences provided herein.

Also provided is an isolated nucleic acid encoding a single-chain variable fragment (scFv) comprising a heavy chain variable region encoded by the polynucleotide sequence set forth in SEQ ID NO: 8; and/or a light chain variable region encoded by the polynucleotide sequence set forth in SEQ ID NO: 10. The heavy chain variable region and the light chain variable region are separated by a linker. In certain embodiments, the linker comprises the amino acid sequence set forth in SEQ ID NO. 15.

Also provided is an isolated nucleic acid encoding a single-chain variable fragment (scFv), wherein the nucleic acid comprises the polynucleotide sequence set forth in SEQ ID NO: 12 or 14. Also provided is an isolated nucleic acid encoding a single-chain variable fragment (scFv), wherein the nucleic acid consists of the polynucleotide sequence set forth in SEQ ID NO: 12 or 14.

Tolerable variations of the nucleic acid sequences will be known to those of skill in the art. For example, in some embodiments the nucleic acid comprises a nucleotide sequence that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any of the nucleotide sequences set forth in SEQ ID NO: 8, 10, 12, or 14.

In certain embodiments, a nucleic acid of the present disclosure comprises a first polynucleotide sequence and a second polynucleotide sequence. In certain embodiments, the first polynucleotide sequence comprises a polynucleotide sequence encoding a FAP-targeting binding polypeptide of the present disclosure. In some embodiments, the FAP-targeting binding polypeptide of the present disclosure may be employed in combination with other therapeutic agents, for example, without limitation, immunotherapies such as immuno-oncology antibody therapy and checkpoint blockade, or CAR-T cell therapies. Accordingly, in such embodiments, the second polynucleotide sequence may comprise a polynucleotide sequence encoding for an anti-cancer antibody, a checkpoint blockage molecule, or a CAR.

The first and second polynucleotide sequence may be separated by a linker. For example, in certain embodiments the heavy chain variable region and the light chain variable region of an scFv are separated by a linker. In certain embodiments, the linker comprises the amino acid sequence set forth in SEQ ID NO. 15. A linker for use in the present disclosure allows for multiple proteins to be encoded by the same nucleic acid sequence (e.g., a multicistronic or bicistronic sequence), which are translated as a polyprotein that is dissociated into separate protein components. In certain embodiments, the nucleic acid comprises from 5' to 3' the first polynucleotide sequence, the linker, and the second polynucleotide sequence. In certain embodiments, the nucleic acid comprises from 5' to 3' the second polynucleotide sequence, the linker, and the first polynucleotide sequence.

In some embodiments, the linker comprises a nucleic acid sequence that encodes for an internal ribosome entry site (IRES). As used herein, "an internal ribosome entry site" or "IRES" refers to an element that promotes direct internal ribosome entry to the initiation codon, such as ATG, of a protein coding region, thereby leading to cap-independent translation of the gene. Various internal ribosome entry sites are known to those of skill in the art, including, without limitation, IRES obtainable from viral or cellular mRNA sources, e.g., immunoglobulin heavy-chain binding protein (BiP); vascular endothelial growth factor (VEGF); fibroblast growth factor 2; insulin-like growth factor; translational initiation factor eIF4G; yeast transcription factors TFIID and HAP4; and IRES obtainable from, e.g., cardiovirus, rhinovirus, aphthovirus, HCV, Friend murine leukemia virus (FrMLV), and Moloney murine leukemia virus (MoMLV). Those of skill in the art would be able to select the appropriate IRES for use in the present invention.

In some embodiments, the linker comprises a nucleic acid sequence that encodes for a self-cleaving peptide. As used herein, a "self-cleaving peptide" or "2A peptide" refers to an oligopeptide that allow multiple proteins to be encoded as polyproteins, which dissociate into component proteins upon translation. Use of the term "self-cleaving" is not intended to imply a proteolytic cleavage reaction. Various self-cleaving or 2A peptides are known to those of skill in the art, including, without limitation, those found in members of the Picornaviridae virus family, e.g., foot-and-mouth disease virus (FMDV), equine rhinitis A virus (ERAV0, *Thosea asigna* virus (TaV), and porcine tescho virus-1 (PTV-1); and carioviruses such as Theilovirus and encephalomyocarditis viruses. 2A peptides derived from FMDV, ERAV, PTV-1, and TaV are referred to herein as "F2A," "E2A," "P2A," and "T2A," respectively. Those of skill in the art would be able to select the appropriate self-cleaving peptide for use in the present invention.

In some embodiments, a linker further comprises a nucleic acid sequence that encodes a furin cleavage site. Furin is a ubiquitously expressed protease that resides in the trans-golgi and processes protein precursors before their secretion. Furin cleaves at the COOH-terminus of its consensus recognition sequence. Various furin consensus recognition sequences (or "furin cleavage sites") are known to those of skill in the art, including, without limitation, Arg-X1-Lys-Arg (SEQ ID NO:32) or Arg-X1-Arg-Arg (SEQ ID NO:33), X2-Arg-X1-X3-Arg (SEQ ID NO:34) and Arg-X1-X1-Arg (SEQ ID NO:35), such as an Arg-Gln-Lys-Arg (SEQ ID NO:36), where X1 is any naturally occurring amino acid, X2 is Lys or Arg, and X3 is Lys or Arg. Those of skill in the art would be able to select the appropriate Furin cleavage site for use in the present invention.

In some embodiments, the linker comprises a nucleic acid sequence encoding a combination of a Furin cleavage site and a 2A peptide. Examples include, without limitation, a linker comprising a nucleic acid sequence encoding a Furin cleavage site and F2A, a linker comprising a nucleic acid sequence encoding a Furin cleavage site and E2A, a linker comprising a nucleic acid sequence encoding a Furin cleavage site and P2A, a linker comprising a nucleic acid sequence encoding a Furin cleavage site and T2A. Those of skill in the art would be able to select the appropriate combination for use in the present invention. In such embodiments, the linker may further comprise a spacer sequence between the Furin cleavage site and the 2A peptide. In some embodiments, the linker comprises a Furin cleavage site 5' to a 2A peptide. In some embodiments, the linker comprises a 2A peptide 5' to a Furin cleavage site. Various spacer sequences are known in the art, including, without limitation, glycine serine (GS) spacers such as (GS)$_n$, (GSGGS)$_n$ (SEQ ID NO:21) and (GGGS)$_n$ (SEQ ID NO:22), where n represents an integer of at least 1. Exemplary spacer sequences can comprise amino acid sequences including, without limitation, GGSG (SEQ ID NO:24), GGSGG (SEQ ID NO:25), GSGSG (SEQ ID NO:26), GSGGG (SEQ ID NO:27), GGGSG (SEQ ID NO:28), GSSSG (SEQ ID NO:29), and the like. Those of skill in the art would be able to select the appropriate spacer sequence for use in the present invention.

Another aspect of the invention provides a vector comprising any one of the isolated nucleic acids disclosed herein. In certain embodiments, the vector is selected from the group consisting of a DNA vector, an RNA vector, a plasmid, a lentiviral vector, an adenoviral vector, an adeno-associated viral vector, and a retroviral vector. In certain embodiments, the vector is an expression vector.

Also provided is a host cell comprising any of the vectors or nucleic acids disclosed herein. The host cell may be of eukaryotic, prokaryotic, mammalian, or bacterial origin. A method of producing a binding polypeptide or scFv that binds to FAP is also provided herein, wherein the method comprises culturing the host cell.

In some embodiments, a nucleic acid of the present disclosure may be operably linked to a transcriptional control element, e.g., a promoter, and enhancer, etc. Suitable promoter and enhancer elements are known to those of skill in the art.

In certain embodiments, the nucleic acid is in operable linkage with a promoter. In certain embodiments, the promoter is a phosphoglycerate kinase-1 (PGK) promoter.

For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

In some embodiments, the promoter is a CD8 cell-specific promoter, a CD4 cell-specific promoter, a neutrophil-specific promoter, or an NK-specific promoter. For example, a CD4 gene promoter can be used; see, e.g., Salmon et al. Proc. Natl. Acad. Sci. USA (1993) 90:7739; and Marodon et al. (2003) Blood 101:3416. As another example, a CD8 gene promoter can be used. NK cell-specific expression can be achieved by use of an NcrI (p46) promoter; see, e.g., Eckelhart et al. Blood (2011) 117:1565.

For expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GALT promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art. Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, J. Bacteriol. (1991) 173(1): 86-93; Alpuche-Aranda et al., Proc. Natl. Acad. Sci. USA (1992) 89(21): 10079-83), a nirB promoter (Harborne et al. Mol. Micro. (1992) 6:2805-2813), and the like (see, e.g., Dunstan et al., Infect. Immun. (1999) 67:5133-5141; McKelvie et al., Vaccine (2004) 22:3243-3255; and Chatfield et al., Biotechnol. (1992) 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al., Infect. Immun. (2002) 70:1087-1096); an rpsM promoter (see, e.g., Valdivia and Falkow Mol. Microbiol. (1996). 22:367); a tet promoter (see, e.g., Hillen, W. and Wissmann, A. (1989) In Saenger, W. and Heinemann, U. (eds), Topics in Molecular and Structural Biology, Protein—Nucleic Acid Interaction. Macmillan, London, UK, Vol. 10, pp. 143-162); an SP6 promoter (see, e.g., Melton et al., Nucl. Acids Res. (1984) 12:7035); and the like. Suitable strong promoters for use in prokaryotes such as *Escherichia coli* include, but are not limited to Trc, Tac, T5, T7, and PLambda. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, e.g., deBoer et al., Proc. Natl. Acad. Sci. U.S.A. (1983) 80:21-25).

Other examples of suitable promoters include the immediate early cytomegalovirus (CMV) promoter sequence. This promoter sequence is a strong constitutive promoter sequence capable of driving high levels of expression of any polynucleotide sequence operatively linked thereto. Other constitutive promoter sequences may also be used, including, but not limited to a simian virus 40 (SV40) early promoter, a mouse mammary tumor virus (MMTV) or human immunodeficiency virus (HIV) long terminal repeat (LTR) promoter, a MoMuLV promoter, an avian leukemia virus promoter, an Epstein-Barr virus immediate early promoter, a Rous sarcoma virus promoter, the EF-1 alpha promoter, as well as human gene promoters such as, but not limited to, an actin promoter, a myosin promoter, a hemoglobin promoter, and a creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In some embodiments, the locus or construct or transgene containing the suitable promoter is irreversibly switched through the induction of an inducible system. Suitable systems for induction of an irreversible switch are well known in the art, e.g., induction of an irreversible switch may make use of a Cre-lox-mediated recombination (see, e.g., Fuhrmann-Benzakein, et al., Proc. Natl. Acad. Sci. USA (2000) 28:e99, the disclosure of which is incorporated herein by reference). Any suitable combination of recombinase, endonuclease, ligase, recombination sites, etc. known to the art may be used in generating an irreversibly switchable promoter. Methods, mechanisms, and requirements for performing site-specific recombination, described elsewhere herein, find use in generating irreversibly switched promoters and are well known in the art, see, e.g., Grindley et al. Annual Review of Biochemistry (2006) 567-605; and Tropp, Molecular Biology (2012) (Jones & Bartlett Publishers, Sudbury, Mass.), the disclosures of which are incorporated herein by reference.

A nucleic acid of the present disclosure may be present within an expression vector and/or a cloning vector. An expression vector can include a selectable marker, an origin of replication, and other features that provide for replication and/or maintenance of the vector. Suitable expression vectors include, e.g., plasmids, viral vectors, and the like. Large numbers of suitable vectors and promoters are known to those of skill in the art; many are commercially available for generating a subject recombinant construct. The following vectors are provided by way of example, and should not be construed in anyway as limiting: Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest. Opthalmol. Vis. Sci. (1994) 35: 2543-2549; Borras et al., Gene Ther. (1999) 6: 515-524; Li and Davidson, Proc. Natl. Acad. Sci. USA (1995) 92: 7700-7704; Sakamoto et al., H. Gene Ther. (1999) 5: 1088-1097; WO 94/12649, WO 93/03769; WO 93/19191; WO 94/28938; WO 95/11984 and WO 95/00655); adeno-associated virus (see, e.g., Ali et al., Hum. Gene Ther. (1998) 9: 81-86, Flannery et al., Proc. Natl. Acad. Sci. USA (1997) 94: 6916-6921; Bennett et al., Invest. Opthalmol. Vis. Sci. (1997) 38: 2857-2863; Jomary et al., Gene Ther. (1997) 4:683 690, Rolling et al., Hum. Gene Ther. (1999) 10: 641-648; Ali et al., Hum. Mol. Genet. (1996) 5: 591-594; Srivastava in WO 93/09239, Samulski et al., J. Vir. (1989) 63: 3822-3828; Mendelson et al., Virol. (1988) 166: 154-165; and Flotte et al., Proc. Natl. Acad. Sci. USA (1993) 90: 10613-10617); SV40; herpes simplex virus; human immunodeficiency virus (see, e.g., Miyoshi et al., Proc. Natl. Acad. Sci. USA (1997) 94: 10319-23; Takahashi et al., J. Virol. (1999) 73: 7812-7816); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Additional expression vectors suitable for use are, e.g., without limitation, a lentivirus vector, a gamma retrovirus vector, a foamy virus vector, an adeno-associated virus vector, an adenovirus vector, a pox virus vector, a herpes virus vector, an engineered hybrid virus vector, a transposon mediated vector, and the like. Viral vector technology is well known in the art and is described, for example, in Sambrook et al., 2012, Molecular Cloning: A Laboratory Manual, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses.

In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

In some embodiments, an expression vector (e.g., a lentiviral vector) may be used to introduce the nucleic acid into a host cell. Accordingly, an expression vector (e.g., a lentiviral vector) of the present invention may comprise a nucleic acid encoding a polypeptide. In some embodiments, the expression vector (e.g., lentiviral vector) will comprise additional elements that will aid in the functional expression of the polypeptide encoded therein. In some embodiments, an expression vector comprising a nucleic acid encoding for a polypeptide further comprises a mammalian promoter. In one embodiment, the vector further comprises an elongation-factor-1-alpha promoter (EF-1α promoter). Use of an EF-1α promoter may increase the efficiency in expression of downstream transgenes. Physiologic promoters (e.g., an EF-1α promoter) may be less likely to induce integration mediated genotoxicity, and may abrogate the ability of the retroviral vector to transform stem cells. Other physiological promoters suitable for use in a vector (e.g., lentiviral vector) are known to those of skill in the art and may be incorporated into a vector of the present invention. In some embodiments, the vector (e.g., lentiviral vector) further comprises a non-requisite cis acting sequence that may improve titers and gene expression. One non-limiting example of a non-requisite cis acting sequence is the central polypurine tract and central termination sequence (cPPT/CTS) which is important for efficient reverse transcription and nuclear import. Other non-requisite cis acting sequences are known to those of skill in the art and may be incorporated into a vector (e.g., lentiviral vector) of the present invention. In some embodiments, the vector further comprises a posttranscriptional regulatory element. Posttranscriptional regulatory elements may improve RNA translation, improve transgene expression and stabilize RNA transcripts. One example of a posttranscriptional regulatory element is the woodchuck hepatitis virus posttranscriptional regulatory element (WPRE). Accordingly, in some embodiments a vector for the present invention further comprises a WPRE sequence. Various posttranscriptional regulator elements are known to those of skill in the art and may be incorporated into a vector (e.g., lentiviral vector) of the present invention. A vector of the present invention may further comprise additional elements such as a rev response element (RRE) for RNA transport, packaging sequences, and 5' and 3' long terminal repeats (LTRs). The term "long terminal repeat" or "LTR" refers to domains of base pairs located at the ends of retroviral DNAs which comprise U3, R and U5 regions. LTRs generally provide functions required for the expression of retroviral genes (e.g., promotion, initiation and polyadenylation of gene transcripts) and to viral replication. In one embodiment, a vector (e.g., lentiviral vector) of the present invention includes a 3' U3 deleted LTR. Accordingly, a vector (e.g., lentiviral vector) of the present invention may comprise any combination of the elements described herein to enhance the efficiency of functional expression of transgenes. For example, a vector (e.g., lentiviral vector) of the present invention may comprise a WPRE sequence, cPPT sequence, RRE sequence, 5'LTR, 3' U3 deleted LTR' in addition to a nucleic acid encoding for a CAR.

Vectors of the present invention may be self-inactivating vectors. As used herein, the term "self-inactivating vector" refers to vectors in which the 3' LTR enhancer promoter region (U3 region) has been modified (e.g., by deletion or substitution). A self-inactivating vector may prevent viral transcription beyond the first round of viral replication. Consequently, a self-inactivating vector may be capable of infecting and then integrating into a host genome (e.g., a mammalian genome) only once, and cannot be passed further. Accordingly, self-inactivating vectors may greatly reduce the risk of creating a replication-competent virus.

In some embodiments, a nucleic acid of the present invention may be RNA, e.g., in vitro synthesized RNA. Methods for in vitro synthesis of RNA are known to those of skill in the art; any known method can be used to synthesize RNA comprising a sequence encoding a polypeptide of the present disclosure. Methods for introducing RNA into a host cell are known in the art. See, e.g., Zhao et al. Cancer Res. (2010) 15: 9053. Introducing RNA comprising a nucleotide sequence encoding a polypeptide of the present disclosure into a host cell can be carried out in vitro, ex vivo or in vivo. For example, a host cell (e.g., an NK cell, a cytotoxic T lymphocyte, etc.) can be electroporated in vitro or ex vivo with RNA comprising a nucleotide sequence encoding a polypeptide of the present disclosure.

In order to assess the expression of a polypeptide or portions thereof, the expression vector to be introduced into a cell may also contain either a selectable marker gene or a reporter gene, or both, to facilitate identification and selection of expressing cells from the population of cells sought to be transfected or infected through viral vectors. In some embodiments, the selectable marker may be carried on a separate piece of DNA and used in a co-transfection procedure. Both selectable markers and reporter genes may be flanked with appropriate regulatory sequences to enable expression in the host cells. Useful selectable markers include, without limitation, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assessed at a suitable time after the DNA has been introduced into the recipient cells. Suitable reporter genes may include, without limitation, genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82).

In some embodiments, a nucleic acid of the present disclosure is provided for the production of a polypeptide as described herein, e.g., in a host cell. In some embodiments, a nucleic acid of the present disclosure provides for amplification of the polypeptide-encoding nucleic acid.

D. Methods of Use

The anti-FAP antibodies, binding polypeptides, and scFvs disclosed herein can also be used for diagnostic and imaging applications.

For example, an anti-FAP antibody described herein can be used to assay FAP protein levels in a biological sample using classical immunohistological methods known to those of skill in the art, including immunoassays, such as enzyme linked immunosorbent assay (ELISA), immunoprecipitation, Western blotting, or immunohistochemistry. Suitable antibody assay labels are known in the art and include, but are not limited to, enzyme labels, such as, glucose oxidase, alkaline phosphatase, and horseradish peroxidase; radioisotopes, such as iodine ($^{125}$I, $^{111}$I) carbon ($^{14}$C), sulfur ($^{35}$S), tritium (3H), indium ($^{121}$In), and technetium ($^{99m}$Tc); luminescent labels, such as luminol; and fluorescent labels, such as fluorescein and rhodamine, and biotin. Such labels can be used to label the binding polypeptide, antibody, or an antigen-binding fragment thereof (e.g. scFv) described herein.

Alternatively, a second antibody that recognizes an anti-FAP antibody or antigen-binding fragment thereof described herein can be labeled and used in combination with an anti-FAP antibody or antigen-binding fragment thereof to detect FAP protein levels. In one embodiment, the present invention relates to the use of an anti-FAP antibody of the invention, for assaying and/or detecting FAP protein levels in a biological sample in vitro or in a subject in vivo.

Assaying for the expression level of FAP protein is intended to include qualitatively or quantitatively measuring or estimating the level of a FAP protein in a first biological sample either directly (e.g., by determining or estimating absolute protein level) or relatively (e.g., by comparing to the disease associated protein level in a second biological sample). FAP polypeptide expression level in the first biological sample can be measured or estimated and compared to a standard FAP protein level. The standard can be taken from a second biological sample obtained from an individual not having the disorder or can be determined by averaging levels from a population of individuals not having the disorder. As will be appreciated in the art, once the "standard" FAP polypeptide level is known, it can be used repeatedly as a standard for comparison.

An anti-FAP antibody or antigen-binding fragment thereof described herein can be used for prognostic, diagnostic, monitoring, or screening applications, including in vitro and in vivo applications well known and standard to the skilled artisan and based on the present description.

Prognostic, diagnostic, monitoring and screening assays and kits for in vitro assessment and evaluation of immune system status and/or immune response may be utilized to predict, diagnose and monitor or evaluate patient samples including those known to have, or suspected of having, an immune system dysfunction, or disease or condition, or with regard to an anticipated or desired immune system response, antigen response or vaccine response related to the treatment of the disease of condition. The assessment and evaluation of immune system status and/or immune response is also useful in determining the suitability of a patient for a clinical trial of a drug or for the administration of a particular chemotherapeutic agent or an antibody or antigen-binding fragment thereof, including combinations thereof, versus a different agent or antibody or antigen-binding fragment thereof. This type of prognostic and diagnostic monitoring and assessment is already in practice utilizing antibodies against the HER2 protein in breast cancer (HercepTest™, Dako) where the assay is also used to evaluate patients for antibody therapy using Herceptin®. In vivo applications include directed cell therapy and immune system modulation and radio imaging of immune responses.

In one aspect, the present invention relates to an anti-FAP antibody and/or pharmaceutical composition of the present invention for use as a diagnostic.

In one aspect, the present invention relates to an anti-FAP antibody and/or pharmaceutical composition of the present invention for use in a method for the prediction, diagnosis and/or monitoring of an immune system-dysfunction and/or cancer.

In one embodiment, the present invention relates to the use of an anti-FAP antibody of the invention, for predicting, diagnosing and/or monitoring an immune system-dysfunction and/or cancer in a subject by assaying and/or detecting FAP protein levels in a biological sample of the subject of in vitro.

In one embodiment, an anti-FAP antibody or antigen-binding fragment thereof can be used in immunohistochemistry of biopsy samples. In another embodiment, an anti-FAP antibody or antigen-binding fragment thereof can be used to detect levels of FAP, or levels of cells which contain FAP on their membrane surface, which levels can then be linked to certain disease symptoms. Anti-FAP antibodies or antigen-binding fragments thereof described herein may carry a detectable or functional label. When fluorescence labels are used, currently available microscopy and fluorescence-activated cell sorter analysis (FACS) or combination of both methods procedures known in the art may be utilized to identify and to quantitate the specific binding members.

Anti-FAP antibodies or antigen-binding fragments thereof described herein may carry a fluorescence label. Exemplary fluorescence labels include, for example, reactive and conjugated probes e.g. Aminocoumarin, Fluorescein and Texas red, Alexa Fluor dyes, Cy dyes and DyLight dyes. An anti-FAP antibody or antigen-binding fragment thereof may carry a radioactive label, such as the isotopes $^{3}$H, $^{14}$C, $^{32}$P, $^{35}$S, $^{36}$Cl, $^{51}$Cr, $^{52}$Co, $^{57}$Co, $^{59}$Fe, $^{67}$Cu, $^{90}$Y, $^{99M}$Tc, $^{111}$In, $^{117}$Lu, $^{121}$I, $^{124}$I, $^{125}$I, $^{131}$I, $^{198}$Au, $^{211}$At, $^{213}$Bi, $^{225}$Ac and $^{186}$Re. When radioactive labels are used, currently available counting procedures known in the art may be utilized to identify and quantitate the specific binding of anti-FAP antibody or antigen-binding fragment thereof to FAP. In the instance where the label is an enzyme, detection may be accomplished by any of the presently utilized colorimetric, spectrophotometric, fluorospectrophotometric, amperometric or gasometric techniques as known in the art. This can be achieved by contacting a sample or a control sample with an anti-FAP antibody or antigen-binding fragment thereof under conditions that allow for the formation of a complex between the antibody or antigen-binding fragment thereof and FAP. Any complexes formed between the antibody or antigen-binding fragment thereof and FAP are detected and compared in the sample and the control. In light of the specific binding of the antibodies described herein for FAP, the antibodies or antigen-binding fragments thereof can be used to specifically detect FAP expression on the surface of cells. The antibodies or antigen-binding fragments thereof described herein can also be used to purify FAP via immune-affinity purification. Also included herein is an assay system which may be prepared in the form of a test kit for the quantitative analysis of the extent of the presence of, for instance, FAP or CTLA-4/FAP ligand complexes. The system or test kit may comprise a labeled component, e.g., a labeled antibody, and one or more additional immunochemical reagents.

In one embodiment, the present invention relates to an in vitro method for assaying and/or detecting FAP protein levels in a biological sample comprising (1) contacting a sample and optionally a control sample with an anti-FAP antibody or antigen-binding fragment thereof of the invention under conditions that allow for the formation of a complex between the antibody or antigen-binding fragment thereof and FAP, and (2) detecting and comparing the complexes formed in the sample and optionally the control.

In certain embodiments, the level and/or distribution of FAP is determined in vivo, (e.g., non-invasively) by detecting an antibody disclosed herein that is detectably labeled using a suitable imaging technique, e.g., positron emission tomography (PET) scan. For example, target antibody-PET or immune-PET (e.g., an anti-FAP PET) can be used to detect the level and/or distribution (e.g., tumor localization) of the target FAP-expressing cells in vivo. Techniques for antibody imaging (e.g., antibody-PET imaging) are known in the art, e.g., as described by Lamberts, L. E. et al. (2015) J. Clin. Oncol. 33 (DOI: 10.1200/JCO.2014.57.8278); Tavare, R. et al. (2014) PNAS 111(3):1108-1113; Pampaloni et al., J Clin Oncol 32:5s, 2014 (suppl; abstr 3084); and Boerman and Oyen (2011) The Journal of Nuclear Medicine 52 (8):1171-72; U.S. Pat. Nos. 5,192,525, 5,219,548, 5,399,338; all of which are incorporated herein by reference.

In one embodiment, the level and/or distribution of FAP is determined in vivo, e.g., by detecting an anti-FAP antibody detectably labeled with a PET reagent, e.g., conjugated to 5-2-(4-isothiocyanatobenzyl)-1,4,7-triazacyclononane-1,4,7-triacetic acid for $^{64}Cu$ radiolabeling, e.g., as described in Tavare, R. et al. (2014) PNAS 111(3):1108-1113. In another embodiment, the level and/or distribution of FAP is determined in vivo, e.g., by detecting an anti-FAP antibody detectably labeled with a PET reagent, e.g., fluorine-18 labeling of the antibody, antibody fragment, or FAP targeting polypeptide. In yet another embodiment, the level and/or distribution FAP is determined in vivo, e.g., by detecting an anti-FAP antibody detectably labeled with a PET reagent, e.g., as described in U.S. Pat. No. 9,988,452. In yet another embodiment, the FAP targeting polypeptide is covalently attached to desferoxamine for chelation to appropriate radioisotopes.

In other embodiments, the level of FAP is determined in a sample (e.g., a tumor biopsy) acquired from the subject (e.g., using immunohistochemical techniques).

Also within the scope of the invention are detection reagents. For example, immuno-PET reagents that include an anti-FAP antibody molecule as described herein, are provided. Exemplary labeling reagents include, but are not limited to, astatine-211 (211At), bromine-76 ($^{76}Br$), calcium-47 ($^{47}Ca$), carbon-11 ($^{11}C$), carbon-14 ($^{14}C$), chromium-51 ($^{51}Cr$), cobalt-57 ($^{57}Co$), cobalt-58 ($^{58}Co$), copper-64 ($^{64}Cu$), erbium-169 ($^{169}Er$), fluorine-18 ($^{18}F$), fluorodeoxyglucose ($^{18}F$-FDG), gallium-67 ($^{67}Ga$), gallium-68 ($^{68}Ga$), hydrogen-3 ($^{3}H$), indium-111 ($^{111}In$), iodine-123 ($^{123}I$), iodine-124 ($^{124}I$), iodine-125 ($^{125}I$), iodine-131 ($^{131}I$), iron-59 ($^{59}Fe$), krypton-81m ($^{81m}Kr$), lutetium-177 ($^{177}Lu$), nitrogen-13 ($^{13}N$), oxygen-15 ($^{15}O$), phosphorus-32 ($^{32}P$), samarium-153 ($^{153}Sm$), selenium-75 ($^{75}Se$), strontium-89 ($^{89}Sr$), thallium-201 ($^{201}Tl$), sodium-22 ($^{22}Na$), sodium-24 ($^{24}Na$), technetium 99m ($^{99m}Tc$), xenon-133 ($^{133}Xe$), yttrium-86 ($^{86}Y$), yttrium-88 ($^{88}Y$), Yttrium-90 ($^{90}Y$), and zirconium-89 ($^{89}Zr$). Additional exemplary labeling reagents and their applications in immune-PET are described, e.g., in Lamberts, L. E. et al. (2015) J. Clin. Oncol. 33 (DOI: 10.1200/JCO.2014.57.8278) and Boerman and Oyen (2011) The Journal of Nuclear Medicine 52 (8):1171-72.

In one aspect, the invention provides a method for identifying a subject suitable for an adoptive cell therapy directed to Fibroblast Activation Protein (FAP). The method comprises (a) isolating a diseased tissue from the subject, (b) contacting the isolated tissue with a binding polypeptide that specifically binds FAP, and (c) detecting FAP-expressing cells in the isolated tissue, thereby identifying a suitable subject for the adoptive cell therapy.

In certain embodiments, the binding polypeptide comprises a heavy chain variable region that comprises three heavy chain complementarity determining regions (HCDRs), wherein HCDR1 comprises the amino acid sequence GYTITSYSLH (SEQ ID NO: 17), HCDR2 comprises the amino acid sequence EINPANGDHNFSEKFEIK (SEQ ID NO: 2), and HCDR3 comprises the amino acid sequence LDDSRFHWYFDV (SEQ ID NO: 3); and a light chain variable region that comprises three light chain complementarity determining regions (LCDRs), wherein LCDR1 comprises the amino acid sequence TASSSVSYMY (SEQ ID NO: 4), a LCDR2 comprises the amino acid sequence LTSNLAS (SEQ ID NO: 20), and LCDR3 comprises the amino acid sequence QQWSGYPPIT (SEQ ID NO: 6).

In certain embodiments, the isolated binding polypeptide comprises a heavy chain variable region that comprises three heavy chain complementarity determining regions (HCDRs), wherein HCDR1 comprises the amino acid sequence YTITSYSLH (SEQ ID NO: 1), and/or HCDR2 comprises the amino acid sequence EINPANGDHNFSEKFEIK (SEQ ID NO: 2), and/or HCDR3 comprises the amino acid sequence LDDSRFHWYFDV (SEQ ID NO: 3); and a light chain variable region that comprises three light chain complementarity determining regions (LCDRs), wherein LCDR1 comprises the amino acid sequence TASSSVSYMY (SEQ ID NO: 4), and/or LCDR2 comprises the amino acid sequence LTSNLA (SEQ ID NO: 5), and/or LCDR3 comprises the amino acid sequence QQWSGYPPIT (SEQ ID NO: 6).

In certain embodiments, the isolated binding polypeptide comprises a heavy chain variable region that comprises three heavy chain complementarity determining regions (HCDRs), wherein HCDR1 comprises the amino acid sequence GYTITSYSLH (SEQ ID NO: 17), and/or HCDR2 comprises the amino acid sequence EINPANGDHNFSEKFEIK (SEQ ID NO: 2), and/or HCDR3 comprises the amino acid sequence LDDSRFHWYFDV (SEQ ID NO: 3); and a light chain variable region that comprises three light chain complementarity determining regions (LCDRs), wherein LCDR1 comprises the amino acid sequence TASSSVSYMY (SEQ ID NO: 4), and/or LCDR2 comprises the amino acid sequence LTSNLAS (SEQ ID NO: 20), and/or LCDR3 comprises the amino acid sequence QQWSGYPPIT (SEQ ID NO: 6).

In certain embodiments, the isolated binding polypeptide comprises a heavy chain variable region that comprises three heavy chain complementarity determining regions (HCDRs), wherein HCDR1 comprises the amino acid sequence YTITSYSLH (SEQ ID NO: 1), and/or HCDR2 comprises the amino acid sequence EINPANGDHNFSEKFEIKAT (SEQ ID NO: 18), and/or HCDR3 comprises the amino acid sequence TRLDDSRFHWYFDV (SEQ ID NO: 19); and a light chain variable region that comprises three light chain complementarity determining regions (LCDRs), wherein LCDR1 comprises the amino acid sequence TASSSVSYMY (SEQ ID NO: 4), and/or LCDR2 comprises the amino acid sequence LTSNLA (SEQ ID NO: 5), and/or LCDR3 comprises the amino acid sequence QQWSGYPPIT (SEQ ID NO: 6).

In certain embodiments, the isolated binding polypeptide comprises a heavy chain variable region that comprises any of the three heavy chain complementarity determining regions, HCDR1, HCDR2, and HCDR3, as described herein. In certain embodiments, the antigen-binding domain comprises a light chain variable region that comprises any of the three light chain complementarity determining regions, LCDR1, LCDR2, and LCDR3, as described herein. In certain embodiments, the antigen-binding domain comprises any combination of HCDR1, HCDR2, HCDR3, LCDR1, LCDR2, and LCDR3, and described herein. The skilled artisan would readily be able to determine the relevant complementarity determining regions based on amino acid numbering in view of the heavy and light chain variable region sequences provided herein.

In certain embodiments, the binding polypeptide comprises an antibody or an antigen-binding fragment thereof. In certain embodiments, the antigen-binding fragment is selected from the group consisting of a Fab, a single-chain variable fragment (scFv), or a single-domain antibody. In certain embodiments, the antibody is a full-length antibody. In certain embodiments, the antibody or antigen-binding fragment is a humanized antibody or an antigen-binding fragment thereof. In certain embodiments, the binding polypeptide is conjugated to a therapeutic molecule or a diagnostic molecule. In certain embodiments, the diagnostic molecule comprises a detectable label. In certain embodiments, the detectable label is a radiolabel, a fluorophore, an enzyme, a hapten, biotin, or a chromophore.

In certain embodiments, the subject is administered the adoptive cell therapy after the subject is identified as a suitable subject. In certain embodiments, the adoptive cell therapy comprises a modified immune cell comprising a chimeric antigen receptor (CAR). In certain embodiments, the immune cells are T lymphocytes. In certain embodiments, the immune cells are NK cells. In certain embodiments, the CAR specifically binds to FAP.

In certain embodiments, the binding polypeptide comprises a heavy chain variable region comprising an amino acid sequence having at least 80%, 85%, 90%, 95%, 96%, 96%, 97%, 98%, 99% identity to the amino acid sequence of the heavy chain variable region set forth in SEQ ID NO: 7. In certain embodiments, the binding polypeptide comprises a heavy chain variable region comprising an amino acid sequence set forth in SEQ ID NO: 7. In certain embodiments, the binding polypeptide consists a heavy chain variable region consisting of an amino acid sequence set forth in SEQ ID NO: 7. In certain embodiments, the binding polypeptide comprises a light chain variable region comprising an amino acid sequence having at least 80%, 85%, 90%, 95%, 96%, 97%, 98%, 99% identity to the amino acid sequence set forth in SEQ ID NO: 9. In certain embodiments, the binding polypeptide comprises a light chain variable region comprising an amino acid sequence set forth in SEQ ID NO: 9. In certain embodiments, the binding polypeptide consists of a light chain variable region comprising an amino acid sequence set forth in SEQ ID NO: 9.

E. Methods of Treatment

The antibodies, binding polypeptides, and scFvs described herein may be included in a composition for treating a disease or condition in a subject in need thereof. The composition may include a pharmaceutical composition and further include a pharmaceutically acceptable carrier. A therapeutically effective amount of the pharmaceutical composition may be administered to the subject.

In one aspect, the invention provides a method for treating a cancer in a subject in need thereof. The method comprises administering to the subject an isolated binding polypeptide comprising an antigen-binding domain that specifically binds to an epitope of human and canine, and/or murine fibroblast activation protein (FAP). In certain embodiments, the binding polypeptide comprises any of the HCDRs or LCDRs contemplated herein. In certain embodiments, the binding polypeptide comprises a heavy chain variable region comprising an amino acid sequence at least 80%, 85%, 90%, 95%, 96%, 97%, 98%, 99%, or 100% identical to SEQ ID NO: 7 and/or a light chain variable region comprising an amino acid sequence at least 80%, 85%, 90%, 95%, 96%, 97%, 98%, 99%, or 100% identical to SEQ ID NO: 9.

In certain embodiments, the cancer is associated with fibroblast activation protein (FAP)-expressing cells. In certain embodiments, the FAP-expressing cell is a cancer-associated cell. In certain embodiments, the cancer-associated cell is a cancer-associated fibroblast (CAF). In certain embodiments, the FAP-expressing cancer-associated cell is a FAP-expressing adipocyte. In certain embodiments, the FAP-expressing cancer-associated cell is a tumor-associated macrophage (TAM). In certain embodiments, the FAP-expressing cancer-associated cell is a tumor-associated neutrophil (TAN). In certain embodiments, the FAP-expressing cancer-associated cell is a myeloid-derived suppressor cell (MDSC). In certain embodiments, the FAP-expressing cancer-associated cell is a cancer-initiating cell.

In certain embodiments, the binding polypeptide specifically binds to fibroblast activation protein (FAP). In certain embodiments, the binding polypeptide comprises an antibody or an antigen-binding fragment thereof. In certain embodiments, the antigen-binding fragment is selected from the group consisting of a Fab, a single-chain variable fragment (scFv), or a single-domain antibody. In certain embodiments, the antibody is a full-length antibody. In certain embodiments, the antibody or antigen-binding fragment is a humanized antibody or an antigen-binding fragment thereof.

In some embodiments, the FAP-targeting binding polypeptide of the present disclosure may be employed in combination with other therapeutic agents, for example, without limitation, immunotherapies such as immuno-oncology antibody therapy and checkpoint blockade, or CAR-T therapies. Accordingly, in such embodiments, the second polynucleotide sequence may comprise a polynucleotide sequence encoding for an anti-cancer antibody, a checkpoint blockage molecule, or a CAR.

Another aspect of the invention includes a method for treating cancer in a subject in need thereof comprising (a) identifying the subject as a suitable subject, wherein the identifying comprises (i) isolating a diseased tissue from the subject; (ii) contacting the isolated tissue with a binding polypeptide that specifically binds FAP; and (iii) detecting FAP-expressing cells in the isolated tissue; and (b) administering to the suitable subject adoptive cell therapy comprising a modified T cell comprising a chimeric antigen receptor (CAR) that specifically binds to Fibroblast Activation Protein (FAP).

In another aspect of the invention, provided herein is a method of treating fibrosis. Fibrosis is the formation of excess fibrous connective tissue in an organ or tissue in a reparative or reactive process. This deposition of connective tissue by stimulated fibroblasts can interfere with or completely inhibit the normal architecture and function of the underlying organ or tissue. In certain embodiments, the fibrosis that may be treated include but are not limited to lung fibrosis, cardiac fibrosis, liver fibrosis, skin fibrosis (including keloids and scleroderma), intestinal fibrosis, and kidney fibrosis. In certain embodiments, the fibrosis is cardiac fibrosis.

Compositions of the invention can be administered in dosages and routes and at times to be determined in appropriate pre-clinical and clinical experimentation and trials. Compositions may be administered multiple times at dosages within these ranges. Administration of the compositions may be combined with other methods useful to treat the desired disease or condition as determined by those of skill in the art.

F. Pharmaceutical Compositions and Formulations

Also provided are pharmaceutical composition comprising any one of the binding polypeptides, scFvs, antibodies, or the antigen-binding fragments disclosed herein. Among the compositions are pharmaceutical compositions and formulations for administration, such as for treatment of a disease or disorder. Also provided are therapeutic methods for administering the pharmaceutical compositions to subjects, e.g., patients.

The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered. A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative. In some aspects, the choice of carrier is determined in part by the particular composition and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the composition, preferably those with activities complementary to the composition, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine. The pharmaceutical composition in some embodiments contains the composition in an amount effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the composition, by multiple bolus administrations of the composition, or by continuous infusion administration of the composition.

Formulations include those for oral, intravenous, intraperitoneal, subcutaneous, pulmonary, transdermal, intramuscular, intranasal, buccal, sublingual, or suppository administration. In some embodiments, the composition is administered parenterally. The term "parenteral," as used herein, includes intravenous, intramuscular, subcutaneous, rectal, vaginal, and intraperitoneal administration. In some embodiments, the composition is administered to the subject using peripheral systemic delivery by intravenous, intraperitoneal, or subcutaneous injection. Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyoi (for example, glycerol, propylene glycol, liquid polyethylene glycol) and suitable mixtures thereof.

Sterile injectable solutions can be prepared by incorporating the composition in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

G. Embodiments of the Disclosure

In one aspect, the invention provides an isolated binding polypeptide comprising an antigen-binding domain that specifically binds to an epitope of human and canine, and/or murine fibroblast activation protein (FAP).

In certain embodiments, the antigen-binding domain comprises: a heavy chain variable region that comprises three heavy chain complementarity determining regions (HCDRs), wherein HCDR1 comprises the amino acid sequence YTITSYSLH (SEQ ID NO: 1), HCDR2 comprises the amino acid sequence EINPANGDHNFSEKFEIK (SEQ ID NO: 2), and HCDR3 comprises the amino acid sequence LDDSRFHWYFDV (SEQ ID NO: 3); and a light chain variable region that comprises three light chain complementarity determining regions (LCDRs), wherein LCDR1 comprises the amino acid sequence TASSSVSYMY (SEQ ID NO: 4), a LCDR2 comprises the amino acid sequence LTSNLA (SEQ ID NO: 5), and LCDR3 comprises the amino acid sequence QQWSGYPPIT (SEQ ID NO: 6).

In certain embodiments, the binding polypeptide binds a fibroblast activation protein (FAP). In certain embodiments, binding polypeptide comprises an antibody or an antigen-binding fragment thereof. In certain embodiments, the antigen-binding fragment is selected from the group consisting of a Fab, a single-chain variable fragment (scFv), or a single-domain antibody. In certain embodiments, the antibody is a full-length antibody. In certain embodiments, the antibody or antigen-binding fragment is a humanized antibody or an antigen-binding fragment thereof.

In certain embodiments, the binding polypeptide comprises a heavy chain variable region comprising an amino acid sequence having at least 80%, 85%, 90%, 95%, 96%, 96%, 97%, 98%, 99% identity to the amino acid sequence of the heavy chain variable region set forth in SEQ ID NO: 7. In certain embodiments, the binding polypeptide comprises a heavy chain variable region comprising an amino acid sequence set forth in SEQ ID NO: 7. In certain embodiments, the binding polypeptide consists of a heavy chain variable region consisting of an amino acid sequence set forth in SEQ ID NO: 7.

In certain embodiments, the binding polypeptide comprises a light chain variable region comprising an amino acid sequence having at least 80%, 85%, 90%, 95%, 96%, 97%, 98%, 99% identity to the amino acid sequence set forth in SEQ ID NO: 9. In certain embodiments, the binding polypeptide comprises a light chain variable region comprising an amino acid sequence set forth in SEQ ID NO: 9. In certain embodiments, the binding polypeptide consists of a light chain variable region comprising an amino acid sequence set forth in SEQ ID NO: 9.

In another aspect, the invention provides an isolated binding polypeptide comprising: a heavy chain variable region comprising the amino acid sequence set forth in SEQ ID NO: 7; and a light chain variable region comprising the amino acid sequence set forth in SEQ ID NO: 9.

In another aspect, the invention provides a single-chain variable fragment (scFv) comprising an antigen-binding domain that specifically binds to an epitope of human and canine, and/or murine fibroblast activation protein (FAP).

In certain embodiments of the scFv, the antigen-binding domain comprises: a heavy chain variable region that comprises three heavy chain complementarity determining regions (HCDRs), wherein HCDR1 comprises the amino acid sequence YTITSYSLH (SEQ ID NO: 1), HCDR2 comprises the amino acid sequence EINPANGDHNFSEKFEIK (SEQ ID NO: 2), and HCDR3 comprises the amino acid sequence LDDSRFHWYFDV (SEQ ID NO: 3); and a light chain variable region that comprises three light chain complementarity determining regions (LCDRs), wherein LCDR1 comprises the amino acid sequence TASSSVSYMY (SEQ ID NO: 4), a LCDR2 comprises the amino acid sequence LTSNLA (SEQ ID NO: 5), and LCDR3 comprises the amino acid sequence QQWSGYPPIT (SEQ ID NO: 6), wherein the heavy chain variable region and the light chain variable region are separated by a linker.

In another aspect, the invention provides a single-chain variable fragment (scFv) comprising a heavy chain variable region comprising the amino acid sequence set forth in SEQ ID NO: 7; and a light chain variable region comprising the amino acid sequence set forth in SEQ ID NO: 9, wherein the heavy chain variable region and the light chain variable region are separated by a linker.

In certain embodiments of the scFv, the linker comprises the amino acid sequence set forth in SEQ ID NO: 15.

In another aspect, the invention provides a single chain variable fragment (scFv) comprising an amino acid sequence set forth in SEQ ID NOs: 11 or 13. In another aspect, the invention provides a single chain variable fragment (scFv) consisting of an amino acid sequence set forth in SEQ ID NOs: 11 or 13.

In another aspect, the invention provides an isolated nucleic acid encoding any of the binding polypeptides or any of the scFvs contemplated herein.

In another aspect, the invention provides an isolated nucleic acid encoding a binding polypeptide comprising an antigen-binding domain that specifically binds an epitope of human and canine, and/or murine Fibroblast Activation Protein (FAP).

In certain embodiments of the nucleic acid, the antigen binding domain comprises a heavy chain variable region that comprises three heavy chain complementarity determining regions (HCDRs), wherein HCDR1 comprises the amino acid sequence YTITSYSLH (SEQ ID NO: 1), HCDR2 comprises the amino acid sequence EINPANGDHNFSEK-FEIK (SEQ ID NO: 2), and HCDR3 comprises the amino acid sequence LDDSRFHWYFDV (SEQ ID NO: 3); and a light chain variable region that comprises three light chain complementarity determining regions (LCDRs), wherein LCDR1 comprises the amino acid sequence TASSSVSYMY (SEQ ID NO: 4), LCDR2 comprises the amino acid sequence LTSNLA (SEQ ID NO: 5), and LCDR3 comprises the amino acid sequence QQWSGYPPIT (SEQ ID NO: 6).

In certain embodiments of the nucleic acid, the binding polypeptide comprises an antibody or an antigen-binding fragment thereof. In certain embodiments of the nucleic acid, the antigen-binding fragment is selected from the group consisting of a Fab, a single-chain variable fragment (scFv), or a single-domain antibody. In certain embodiments of the nucleic acid, the antibody is a full-length antibody. In certain embodiments of the nucleic acid, the antibody or antigen-binding fragment is a humanized antibody or a fragment thereof.

In certain embodiments of the nucleic acid, the heavy chain variable region is encoded by a nucleic acid comprising a polynucleotide sequence having at least 80%, 85%, 90%, 95%, 96%, 96%, 97%, 98%, 99% identity to SEQ ID NO: 8. In certain embodiments of the nucleic acid, the heavy chain variable region is encoded by a nucleic acid comprising the polynucleotide sequence set forth in SEQ ID NO: 8. In certain embodiments of the nucleic acid, wherein the heavy chain variable region is encoded by a nucleic acid consisting of the polynucleotide sequence set forth in SEQ ID NO: 8.

In certain embodiments of the nucleic acid, the light chain variable region is encoded by a nucleic acid comprising a polynucleotide sequence having at least 80%, 85%, 90%, 95%, 96%, 96%, 97%, 98%, 99% identity to the amino acid sequence of the light chain variable region set forth in SEQ ID NO: 10. In certain embodiments of the nucleic acid, the light chain variable region is encoded by a nucleic acid comprising the polynucleotide sequence set forth in SEQ ID NO: 10. In certain embodiments of the nucleic acid, the light chain variable region is encoded by a nucleic acid consisting of a polynucleotide sequence set forth in SEQ ID NO: 10.

In another aspect, the invention provides an isolated nucleic acid encoding a binding polypeptide comprising a heavy chain variable region encoded by a nucleic acid sequence comprising the polynucleotide sequence set forth in SEQ ID NO: 8; and a light chain variable region encoded by a nucleic acid sequence comprising the polynucleotide sequence set forth in SEQ ID NO: 10.

In another aspect, the invention provides an isolated nucleic acid encoding a single-chain variable fragment (scFv) comprising a heavy chain variable region that comprises three heavy chain complementarity determining regions (HCDRs), wherein HCDR1 comprises the amino acid sequence YTITSYSLH (SEQ ID NO: 1), HCDR2 comprises the amino acid sequence EINPANGDHNFSEK-FEIK (SEQ ID NO: 2), and HCDR3 comprises the amino acid sequence LDDSRFHWYFDV (SEQ ID NO: 3); and a light chain variable region that comprises three light chain complementarity determining regions (LCDRs), wherein LCDR1 comprises the amino acid sequence TASSSVSYMY (SEQ ID NO: 4), LCDR2 comprises the amino acid sequence LTSNLA (SEQ ID NO: 5), and LCDR3 comprises the amino acid sequence QQWSGYPPIT (SEQ ID NO: 6).

In another aspect, the invention provides an isolated nucleic acid encoding a single-chain variable fragment (scFv) comprising a heavy chain variable region comprising a nucleotide sequence set forth in SEQ ID NO: 8; and a light chain variable region comprising a nucleotide sequence set forth in SEQ ID NO: 10, wherein the heavy chain variable region and the light chain variable region are separated by a linker. In certain embodiments, the linker comprises the amino acid sequence set forth in SEQ ID NO. 15.

In another aspect, the invention provides an isolated nucleic acid encoding a single-chain variable fragment (scFv) comprising a polynucleotide sequence set forth in SEQ ID NOs: 12 or 14. In another aspect, the invention provides an isolated nucleic acid encoding a single-chain variable fragment (scFv) consisting of a polynucleotide sequence set forth in SEQ ID NOs: 12 or 14.

In another aspect, the invention provides a vector comprising any of the isolated nucleic acids contemplated herein. In certain embodiments, the vector is an expression vector. In certain embodiments, the vector is selected from the group consisting of a DNA vector, an RNA vector, a plasmid, a lentiviral vector, an adenoviral vector, an adeno-associated viral vector, and a retroviral vector.

In another aspect, the invention provides a host cell comprising any of the vectors contemplated herein. In certain embodiments, the host cell is of eukaryotic or prokaryotic origin. In certain embodiments, the host cell is of mammalian origin. In certain embodiments, the host cell is of bacterial origin.

In another aspect, the invention provides a method of producing a binding polypeptide or scFv that binds to FAP, the method comprising culturing any of the host cells contemplated herein.

In another aspect, the invention provides a pharmaceutical composition comprising any of the binding polypeptides or any of the scFvs contemplated herein.

In another aspect, the invention provides a pharmaceutical composition comprising any of the antibodies or any of the antigen-binding fragments contemplated herein.

In another aspect, the invention provides a method for identifying a subject suitable for an adoptive cell therapy directed to Fibroblast Activation Protein (FAP), wherein the method comprises: (a) isolating a diseased tissue from the subject; (b) contacting the isolated tissue with a binding polypeptide that specifically binds FAP; and (c) detecting FAP-expressing cells in the isolated tissue, thereby identifying a suitable subject for the adoptive cell therapy.

In certain embodiments of the method, the binding polypeptide comprises a heavy chain variable region that comprises three heavy chain complementarity determining regions (HCDRs), wherein HCDR1 comprises the amino acid sequence YTITSYSLH (SEQ ID NO: 1), HCDR2 comprises the amino acid sequence EINPANGDHNFSEK-FEIK (SEQ ID NO: 2), and HCDR3 comprises the amino acid sequence LDDSRFHWYFDV (SEQ ID NO: 3); and a light chain variable region that comprises three light chain complementarity determining regions (LCDRs), wherein LCDR1 comprises the amino acid sequence TASSSVSYMY (SEQ ID NO: 4), a LCDR2 comprises the amino acid sequence LTSNLA (SEQ ID NO: 5), and LCDR3 comprises the amino acid sequence QQWSGYPPIT (SEQ ID NO: 6).

In certain embodiments, the binding polypeptide comprises an antibody or an antigen-binding fragment thereof. In certain embodiments, the antigen-binding fragment is selected from the group consisting of a Fab, a single-chain variable fragment (scFv), or a single-domain antibody. In certain embodiments, the antibody is a full-length antibody. In certain embodiments, the antibody or antigen-binding fragment is a humanized antibody or an antigen-binding fragment thereof.

In certain embodiments, the binding polypeptide is conjugated to a therapeutic molecule or a diagnostic molecule. In certain embodiments, the diagnostic molecule comprises a detectable label. In certain embodiments, the detectable label is a radiolabel, a fluorophore, an enzyme, a hapten, biotin, or a chromophore.

In certain embodiments, the subject is administered the adoptive cell therapy after the subject is identified as a suitable subject. In certain embodiments, the adoptive cell therapy comprises a modified immune cell comprising a chimeric antigen receptor (CAR).

In certain embodiments, the immune cells are T lymphocytes. In certain embodiments, the immune cells are NK cells.

In certain embodiments, the CAR specifically binds to FAP.

In certain embodiments, the binding polypeptide comprises a heavy chain variable region comprising an amino acid sequence having at least 80%, 85%, 90%, 95%, 96%, 96%, 97%, 98%, 99% identity to the amino acid sequence of the heavy chain variable region set forth in SEQ ID NO: 7. In certain embodiments, the binding polypeptide comprises a heavy chain variable region comprising an amino acid sequence set forth in SEQ ID NO: 7. In certain embodiments, the binding polypeptide consists a heavy chain variable region consisting of an amino acid sequence set forth in SEQ ID NO: 7.

In certain embodiments, the binding polypeptide comprises a light chain variable region comprising an amino acid sequence having at least 80%, 85%, 90%, 95%, 96%, 97%, 98%, 99% identity to the amino acid sequence set forth in SEQ ID NO: 9. In certain embodiments, the binding polypeptide comprises a light chain variable region comprising an amino acid sequence set forth in SEQ ID NO: 9. In certain embodiments, the binding polypeptide consists of a light chain variable region comprising an amino acid sequence set forth in SEQ ID NO: 9.

In another aspect, the invention provides a method for treating a cancer in a subject in need thereof. The method comprises administering to the subject an isolated binding polypeptide comprising a heavy chain variable region comprising an amino acid sequence at least 80%, 85%, 90%, 95%, 96%, 97%, 98%, 99%, or 100% identical to SEQ ID NO: 7; and a light chain variable region comprising an amino acid sequence at least 80%, 85%, 90%, 95%, 96%, 97%, 98%, 99%, or 100% identical to SEQ ID NO: 9.

In certain embodiments, the cancer is associated with fibroblast activation protein (FAP)-expressing cells. In certain embodiments, the FAP-expressing cell is a cancer-associated cell. In certain embodiments, the cancer-associated cell is a cancer-associated fibroblast (CAF). In certain embodiments, the FAP-expressing cancer-associated cell is a FAP-expressing adipocyte. In certain embodiments, the FAP-expressing cancer-associated cell is a tumor-associated macrophage (TAM). In certain embodiments, the FAP-expressing cancer-associated cell is a tumor-associated neutrophil (TAN). In certain embodiments, the FAP-expressing cancer-associated cell is a myeloid-derived suppressor cell (MDSC). In certain embodiments, the FAP-expressing cancer-associated cell is a cancer-initiating cell.

In certain embodiments, the binding polypeptide specifically binds to fibroblast activation protein (FAP). In certain embodiments, the binding polypeptide comprises an antibody or an antigen-binding fragment thereof. In certain embodiments, antigen-binding fragment is selected from the group consisting of a Fab, a single-chain variable fragment (scFv), or a single-domain antibody. In certain embodiments, the antibody is a full-length antibody. In certain embodiments, the antibody or antigen-binding fragment is a humanized antibody or an antigen-binding fragment thereof.

In another aspect, the invention provides a method for treating cancer in a subject in need thereof, comprising: (a) identifying the subject as a suitable subject, wherein the identifying comprises (i) isolating a diseased tissue from the subject; (ii) contacting the isolated tissue with a binding polypeptide that specifically binds FAP; and (iii) detecting FAP-expressing cells in the isolated tissue; and (b) administering to the suitable subject adoptive cell therapy comprising a modified T cell comprising a chimeric antigen receptor (CAR) that specifically binds to Fibroblast Activation Protein (FAP).

While the present invention has been described with reference to the specific embodiments thereof, it should be understood by those skilled in the art that various changes may be made and equivalents may be substituted without departing from the true spirit and scope of the invention. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present invention. All such modifications are intended to be within the scope of the claims appended hereto. Having now described certain embodiments in detail, the same will be more clearly understood by reference to the following examples, which are included for purposes of illustration only and are not intended to be limiting.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The Materials and Methods used in the performance of the experiments disclosed herein are now described.

Bioinformatic deduction of the canine FAP gene sequence: PCR primers were designed using the NCBI predicted sequence for Canine FAP (XM_005640252.2). The resulting PCR product matched the predicted sequence 100% at the protein level. There were two conservative base pair substitutions at T127 and A603 at the nucleotide level.

Canine FAP cDNA PCR, sub-cloning, and expression: Confluent 10 cm dishes of endogenous FAP expressing canine SK osteosarcoma cells were treated with 1 ml TRIzol (Life Technologies, #15596-026) and total RNA was extracted as per the manufacturer protocol. Using the SuperScript First Strand Synthesis Kit (Life Technologies, #11904-018) cDNA was reverse transcribed from 5 μg of total RNA. This cDNA was used as a template for touchdown PCR with the following primers: forward 5' ATGTA-GACGTGGTTAAAAATTG (SEQ ID NO: 37); reverse 5' CGTCATCTTCAGTCGGACAA (SEQ ID NO: 38). The 2291 bp amplicon was detected on a 1% agarose gel.

The resulting PCR product was purified and cloned into pGEM-T Easy (Promega) and sequenced. This shuttle vector is linearized and contains single "T" overhangs. This allows for simple non-directional cloning of the PCR product by making use of the 3' "A" overhang added to the PCR product by Taq polymerase. From here, the cDNA was cloned into plasmid pcDNA3.1 non-directionally using the EcoRI cloning site.

Canine FAP cDNA was subcloned into lentiviral plasmid (pLenti6/v5-D-TOPO) from pcDNA3.1 using SpeI to excise the cDNA and using XbaI to open pLenti6/v5-D-TOPO. These restriction sites have compatible ends. This resulted in CanineFAP.pLenti6/v5-D-TOPO CanineFAP.pLenti/v5-D-TOPO was co-transfected with packaging plasmids (pMD2.G, pCMVAR8.2) into HEK 293 cells. Virus-containing supernatant was harvested 48 hours later. The viral titer was determined by p24 ELISA and Balb/C 3T3 fibroblasts were transduced at different MOI's ranging from 0.5:1 to 10:1.

Expression of the transgene in Balb/C 3T3.canine FAP cells was confirmed using flow cytometry. The primary antibody used was biotinylated sheep anti-huFAP polyclonal antibody (5 g/ml) from R&D systems. The secondary was APC-Streptavidin (1 µg/ml) from Biolegend.

Immunization and hybridoma generation: Balb/C 3T3 cells expressing full-length canine FAP were used to immunize 14 week old Balb/C.FAP$^{-/-}$ mice. All injections were given intraperitoneally and consisted of 1×10$^7$ cells in 0.5 ml sterile PBS. An initial immunization was followed by boosts on days 14 and 28; animals were then bled on day 42 followed a boost on day 56, bleeding on day 63, and three more boosts on days 70, 217, and 238. On day 241, 2017 spleens were harvested, a single cell suspension prepared, and splenocytes fused with sp2/0 cells by the UPENN Hybridoma Core Facility. Hyridomas supernatants were initially screened by FACS on MC KOSA parental (FAP null) vs. canine FAP-transgene expressing MC KOSA.K9FAP using hybridoma supernatants as the primary antibodies and AF488 goat anti-mouse IgG as a secondary. Clone 4G5 identified as reactive to transduced cells but not parental cells and screened on additional cells to confirm reactivity with FAP expressing but not FAP-negative cells: Human primary fibroblasts, BALB/c 3T3 expressing murine or human FAP transgenes, canine primary fibroblasts, SK KOSA (FAP expressing), and BALB/c 3T3 (FAP negative) cells. 4G5 was then determined to be an IgG1k isotype antibody using (Thermo Fisher Rapid ELISA Mouse mAb Isotyping Kit #37503)

Figure 1:
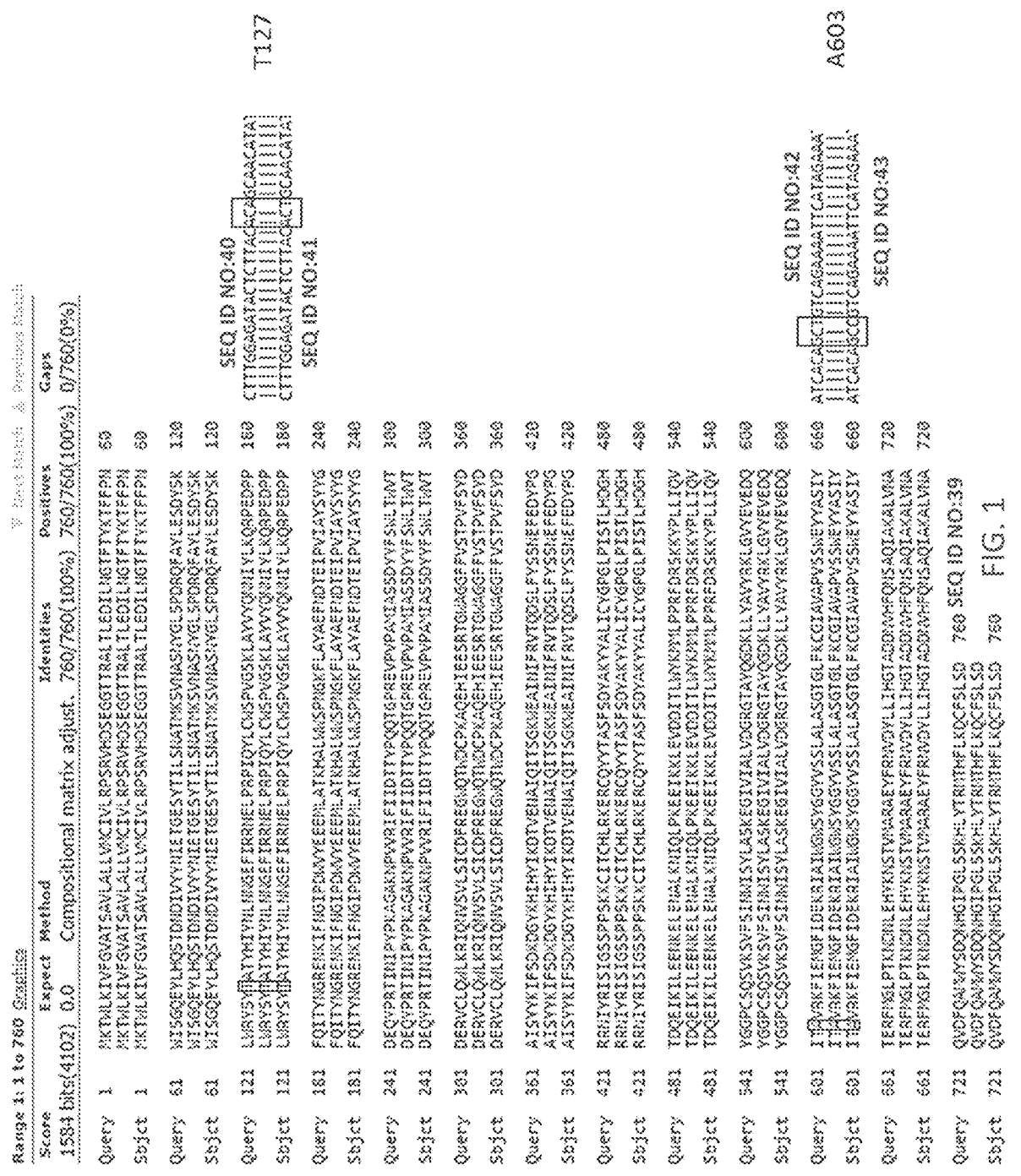

Example 1: Bioinformatic Deduction of Canine FAP Gene Sequence Used to Design PCR Primers As a first step, the sequence of the canine FAP gene was amplified via PCR. PCR primers specific for canine FAP were designed using the NCBI predicted sequence for Canine FAP (XM_005640252.2). The resulting PCR product matched the sequence of canine FAP 100% at the protein level (FIG. 1). Subsequent sequencing revealed canine FAP to possess two conservative base pair substitutions at T127 and A603 at the nucleotide level.

Example 2: Canine FAP cDNA PCR, Subcloning Sequencing and Expression

Figure 2C:
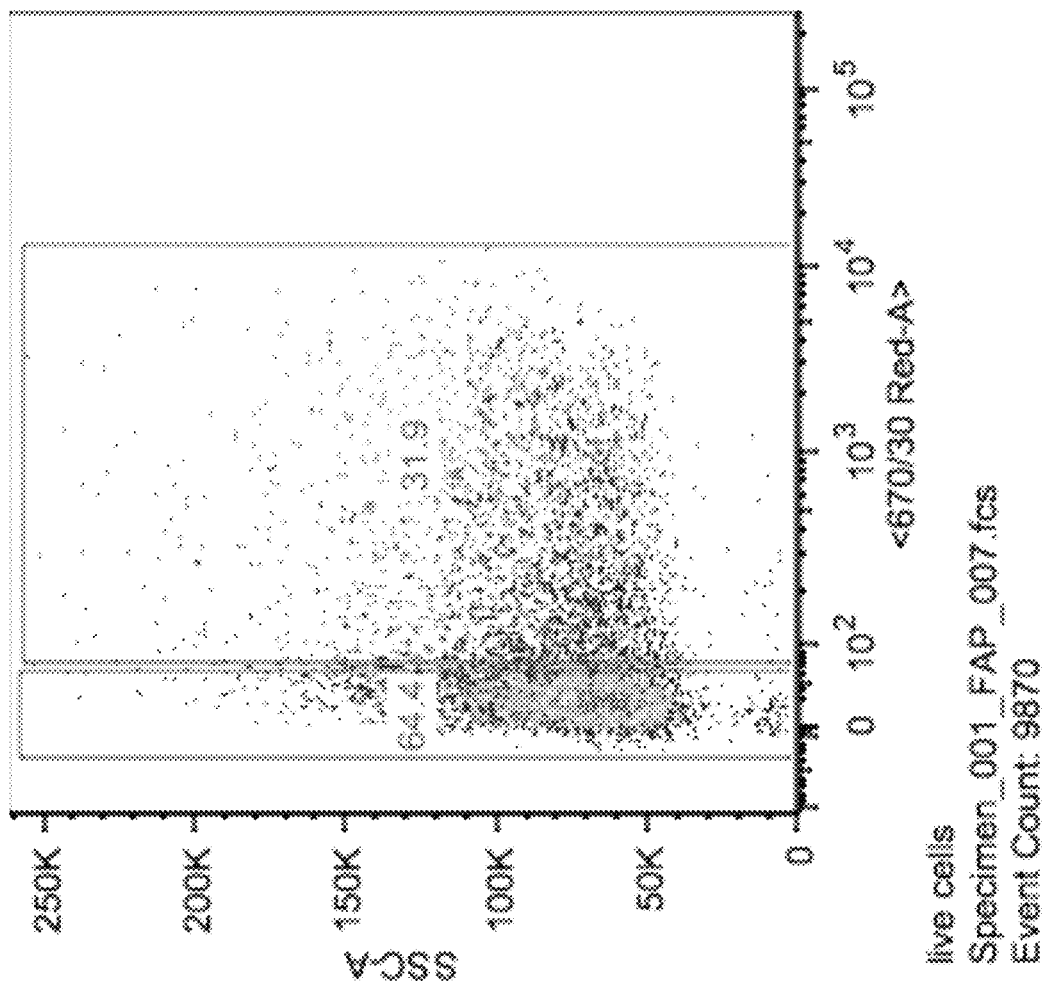

As a first step toward generating an anti-canine FAP antibody, a construct capable of generating recombinant canine FAP protein was created. To provide canine FAP cDNA, endogenous FAP expressing canine SK osteosarcoma cells were subjected to TRIzol-based RNA extraction followed by reverse transcription of the isolated RNA into cDNA. This cDNA was used as a template for touchdown PCR, which resulted in a 2291 bp amplicon. The amplified PCR product was PCR product was purified and cloned into a shuttle vector, which allowed for simple non-directional cloning of the PCR product. From here, the cDNA was cloned into a eukaryotic expression plasmid (FIG. 2A). Canine FAP cDNA was then sub-cloned into a lentiviral plasmid to allow for transduction into mammalian cell lines (FIG. 2B). The resulting canine FAP-lentivirus construct was then co-transfected with packaging plasmids into HEK 293 cells. Virus-containing supernatant was then harvested 48 hours later. The viral titer was determined by p24 ELISA and BALB/c-derived 3T3 fibroblast cells were transduced at various MOIs ranging from 0.5:1 to 10:1. Expression of the transgene in 3T3-canine FAP cells was confirmed using flow cytometry (FIG. 2C).

Example 3. Immunization, Fusion, and Screening

Figure 3:
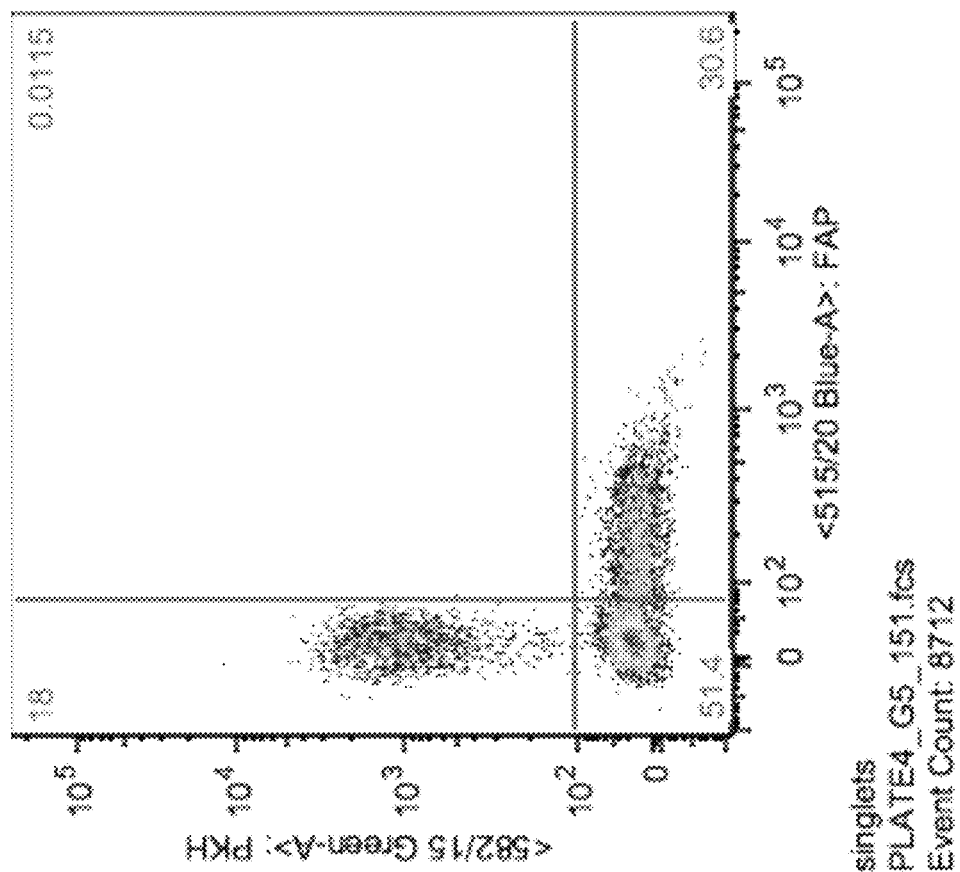
FIG. 3 is a flow cytometry plot demonstrating the generation of anti-FAP antibody producing hybridoma cells. Canine FAP-transduced BALB/c 3T3 cells were used to immunize 14-week-old BALB/c mice. Splenocytes were fused to sp2/0 cells and the resulting hybridomas screened against PKH-labeled MC KOSA parental (FAP null) cells and canine FAP-transgene expressing MC KOSA.K9FAP cells. Primary staining was provided by hybridoma-produced antibody. Secondary staining was performed using a goat anti-mouse IgG secondary antibody followed by readout via flow cytometry.
Figure 5:
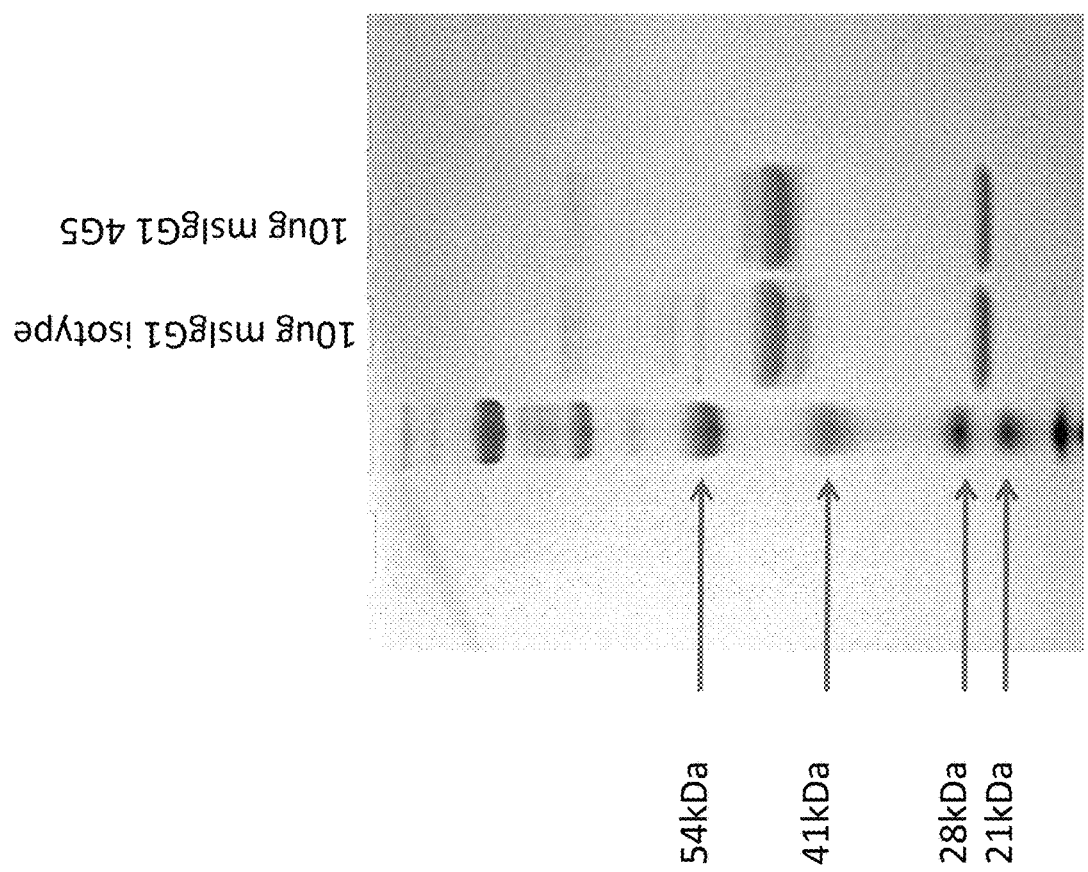
FIG. 5 depicts a protein gel demonstrating that 4G5 antibody and a mouse IgG1 isotype control antibody generate similar banding patterns.

BALB/c 3T3 fibroblast cells transduced to express full-length canine FAP were then used to immunize 14 week old BALB/c FAP$^{-/-}$ mice. All injections were given intraperitoneally and consisted of 1×10$^7$ cells in 0.5 ml sterile PBS. The initial immunization was followed by six booster immunizations at regular intervals over the next eight months. At the conclusion of the study, spleens were harvested, and the resulting single-cell suspensions were used to generate hybridomas via fusion with sp2/0 cells. The resulting hybridomas were then screened for those producing anti-canine FAP antibody. As an initial screen, cells producing immunoglobulin capable of staining canine-FAP transgene-expressing MC KOSA cells, but not FAP null MC KOSA parental cells were identified by flow cytometry (FIG. 3). As a result, the 4G5 clone was identified as a potential candidate. Follow-up studies further revealed that immunoglobulin produced by the clone was able to stain FAP-expressing human primary fibroblasts, BALB/c 3T3 cells expressing murine or human FAP transgenes, canine primary fibroblasts, and FAP-expressing SK KOSA cells. Similarly, 4G5 immunoglobulin was unable to stain FAP-negative parental BALB/c 3T3 cells, further indicating its specificity. Lastly, a commercial ELISA-based antibody isotyping kit was used to further characterize the immunoglobulin produced by 4G5. These results demonstrated that 4G5 is a mouse-IgG1-kappa isotype antibody (FIGS. 4A-4C). Follow-up protein gels comparing 4G5 to a mouse IgG1 isotype control resulted in a similar pattern of heavy and light-chain bands, further demonstrating the isotypic identity of 4G5 (FIG. 5).

OTHER EMBODIMENTS

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments 5 and variations of this invention may be devised by others skilled in the art without departing from the true spirit and scope of the invention. The appended claims are intended to be construed to include all such embodiments and equivalent variations.

What is claimed is:

1. An isolated nucleic acid comprising a nucleic acid sequence encoding an antigen-binding domain that specifically binds to an epitope of a fibroblast activation protein (FAP), wherein the antigen binding domain comprises:
   (a) a heavy chain variable region that comprises a heavy chain complementarity determining region (HCDR) 1 comprising the amino acid sequence YTITSYSLH (SEQ ID NO: 1), a HCDR2 comprising the amino acid sequence EINPANGDHNFSEKFEIK (SEQ ID NO: 2), and a HCDR3 comprising the amino acid sequence LDDSRFHWYFDV (SEQ ID NO: 3); and
   (b) a light chain variable region that comprises a light chain complementarity determining region 1 (LCDRs) comprising the amino acid sequence TASSSVSYMY (SEQ ID NO: 4), a LCDR2 comprising the amino acid sequence LTSNLA (SEQ ID NO: 5), and a LCDR3 comprising the amino acid sequence QQWSGYPPIT (SEQ ID NO: 6).

2. The nucleic acid of claim 1, wherein:
   (a) the heavy chain variable region is encoded by:
      (i) a nucleic acid sequence comprising at least 90%, 95%, 96%, 96%, 97%, 98%, or 99% identity to SEQ ID NO: 8;
      (ii) a nucleic acid sequence comprising the sequence set forth in SEQ ID NO: 8; or
      (iii) a nucleic acid sequence consisting of the sequence set forth in SEQ ID NO: 8; or
   (b) the light chain variable region is encoded by:
      (iv) a nucleic acid sequence comprising at least 90%, 95%, 96%, 96%, 97%, 98%, or 99% identity to SEQ ID NO: 10;
      (v) a nucleic acid sequence comprising the sequence set forth in SEQ ID NO: 10; or
      (vi) a nucleic acid sequence consisting of the sequence set forth in SEQ ID NO: 10.

3. The nucleic acid of claim 1, wherein:
(a) the heavy chain variable region is encoded by:
  (i) a nucleic acid sequence comprising at least 90%, 95%, 96%, 96%, 97%, 98%, or 99% identity to SEQ ID NO: 8;
  (ii) a nucleic acid sequence comprising the sequence set forth in SEQ ID NO: 8; or
  (iii) a nucleic acid sequence consisting of the sequence set forth in SEQ ID NO: 8; and
(b) the light chain variable region is encoded by:
  (iv) a nucleic acid sequence comprising at least 90%, 95%, 96%, 96%, 97%, 98%, or 99% identity to SEQ ID NO: 10;
  (v) a nucleic acid sequence comprising the sequence set forth in SEQ ID NO: 10; or
  (vi) a nucleic acid sequence consisting of the sequence set forth in SEQ ID NO: 10.

4. The nucleic acid of claim 3, wherein:
(a) the heavy chain variable region is encoded by the nucleic acid sequence comprising the sequence set forth in SEQ ID NO: 8; and
(b) the light chain variable region is encoded by the nucleic acid sequence comprising the sequence set forth in SEQ ID NO: 10.

5. The nucleic acid of claim 3, wherein the antigen-binding domain is an antibody, a Fab, or an scFv.

6. The nucleic acid of claim 5, wherein the antibody or the antigen-binding fragment thereof is a full-length antibody.

7. The nucleic acid of claim 1, wherein the nucleic acid sequence:
(a) encodes a single-chain variable fragment (scFv) comprising:
  (i) the heavy chain variable region comprising SEQ ID NOs: 1-3; and
  (ii) the light chain variable region comprising SEQ ID NOs: 4-6;
(b) encodes a single-chain variable fragment (scFv) comprising:
  (i) the heavy chain variable region, wherein the heavy chain variable region comprises the nucleotide sequence set forth in SEQ ID NO: 8; and
  (ii) the light chain variable region, wherein the light chain variable region comprises the nucleotide sequence set forth in SEQ ID NO: 10,
  wherein the heavy chain variable region and the light chain variable region are separated by a linker;
(c) encodes a single-chain variable fragment (scFv), wherein the scFv is encoded by a nucleic acid sequence comprising the sequence set forth in SEQ ID NOs: 12 or 14; or
(d) encodes a single-chain variable fragment (scFv), wherein the scFv is encoded by a nucleic acid sequence consisting of the sequence set forth in SEQ ID NOs: 12 or 14.

8. A vector comprising the isolated nucleic acid of claim 1.

9. A host cell comprising the vector of claim 5.

10. The nucleic acid of claim 1, wherein the antigen-binding domain is an antibody or an antigen-binding fragment thereof, a Fab, or an scFv.

11. The nucleic acid of claim 10, wherein the antibody or the antigen-binding fragment thereof is a full-length antibody.

* * * * *